US011755296B2

(12) United States Patent
Arat et al.

(10) Patent No.: US 11,755,296 B2
(45) Date of Patent: Sep. 12, 2023

(54) COMPUTER DEVICE AND METHOD FOR FACILITATING AN INTERACTIVE CONVERSATIONAL SESSION WITH A DIGITAL CONVERSATIONAL CHARACTER

(71) Applicant: HIA Technologies, Inc., La Crescenta, CA (US)

(72) Inventors: Vacit Arat, La Cañada Flintridge, CA (US); Richard Cardran, Los Angeles, CA (US); Rick King, Kiowa, CO (US)

(73) Assignee: HIA Technologies, Inc., La Crescenta, CA (US)

( * ) Notice: Subject to any disclaimer, the term of this patent is extended or adjusted under 35 U.S.C. 154(b) by 0 days.

(21) Appl. No.: 17/949,942

(22) Filed: Sep. 21, 2022

(65) Prior Publication Data
US 2023/0013286 A1 Jan. 19, 2023

Related U.S. Application Data

(63) Continuation of application No. 16/599,439, filed on Oct. 11, 2019, now Pat. No. 11,455,151.
(Continued)

(51) Int. Cl.
*G06F 8/38* (2018.01)
*G06N 3/006* (2023.01)
(Continued)

(52) U.S. Cl.
CPC ............... *G06F 8/38* (2013.01); *G06F 8/35* (2013.01); *G06N 3/006* (2013.01); *G06T 7/70* (2017.01);
(Continued)

(58) Field of Classification Search
CPC ..... G06F 8/38; G06F 8/35; G06T 7/73; G06T 7/70; G06T 19/006; G16H 80/00;
(Continued)

(56) References Cited

U.S. PATENT DOCUMENTS 9,667,786 B1 5/2017 Dube
9,812,151 B1 11/2017 Amini et al.
(Continued)

OTHER PUBLICATIONS

Treasury Wine Estates, www.LivingWineLabels.com, Website, Nov. 15, 2019, 17 pages, Retrieved from the Internet: https://www.livingwinelabels.com/.

*Primary Examiner* — William D Titcomb
(74) *Attorney, Agent, or Firm* — LEE SULLIVAN SHEA & SMITH LLP

(57) ABSTRACT

Disclosed herein is a software technology for facilitating an interactive conversational session between a user and a digital conversational character. For instance, in one aspect, the disclosed process may involve two primary phases: (1) an authoring phase that involves a first user accessing a content authoring tool to create a given type of visual conversation application that facilitates interactions between a second user and a digital conversational character in an interactive conversational session, and (2) a rendering phase that involves the second user accessing the created visual conversation application to interact with the digital conversational character in an interactive conversational session. In one implementation, accessing the created visual conversation application may involve detecting an object and identifying information associated with the detected object.

20 Claims, 14 Drawing Sheets

Related U.S. Application Data

(60) Provisional application No. 62/902,067, filed on Sep. 18, 2019, provisional application No. 62/828,954, filed on Apr. 3, 2019.

(51) Int. Cl.

| | | |
|---|---|---|
| *G16H 80/00* | (2018.01) | |
| *G10L 15/22* | (2006.01) | |
| *G06T 7/73* | (2017.01) | |
| *G06V 20/64* | (2022.01) | |
| *G06V 30/148* | (2022.01) | |
| *G06T 7/70* | (2017.01) | |
| *G06T 19/00* | (2011.01) | |
| *G06V 20/20* | (2022.01) | |
| *G06F 8/35* | (2018.01) | |

(52) U.S. Cl.
CPC .............. *G06T 7/73* (2017.01); *G06T 19/006* (2013.01); *G06V 20/20* (2022.01); *G06V 20/64* (2022.01); *G06V 30/153* (2022.01); *G10L 15/22* (2013.01); *G16H 80/00* (2018.01)

(58) Field of Classification Search
CPC ...... G06V 20/00; G06V 20/64; G06V 30/153; G06N 3/006; G10L 15/22
USPC .......................................................... 706/11
See application file for complete search history.

(56) References Cited

U.S. PATENT DOCUMENTS

| | | | |
|---|---|---|---|
| 10,181,213 B2 | 1/2019 | Bullivant et al. | |
| 10,531,157 B1* | 1/2020 | Loritsch ................... G06F 3/165 | |
| 10,594,757 B1* | 3/2020 | Shevchenko ......... G10L 15/197 | |
| 10,885,336 B1 | 1/2021 | Davis et al. | |
| 10,936,687 B1 | 3/2021 | Paiz | |
| 11,120,226 B1 | 9/2021 | Nudd et al. | |
| 2002/0065682 A1 | 5/2002 | Goldberg | |
| 2009/0004633 A1 | 1/2009 | Johnson et al. | |
| 2009/0285483 A1 | 11/2009 | Guven et al. | |
| 2012/0066270 A1 | 3/2012 | Kravets | |
| 2014/0019116 A1 | 1/2014 | Lundberg et al. | |
| 2014/0074454 A1* | 3/2014 | Brown .................... G10L 15/08 704/235 |
| 2016/0098936 A1 | 4/2016 | Solomon | |
| 2017/0098051 A1 | 4/2017 | Balram | |
| 2017/0132828 A1 | 5/2017 | Zelenin et al. | |
| 2017/0161450 A1 | 6/2017 | White et al. | |
| 2017/0354383 A1 | 12/2017 | Odessky et al. | |
| 2017/0364766 A1 | 12/2017 | Das et al. | |
| 2018/0114527 A1 | 4/2018 | Zilotti et al. | |
| 2018/0114528 A1 | 4/2018 | Yasavur et al. | |
| 2018/0130372 A1 | 5/2018 | Vinkers et al. | |
| 2018/0144738 A1 | 5/2018 | Yasavur et al. | |
| 2018/0197322 A1 | 7/2018 | Sagar et al. | |
| 2018/0321922 A1 | 11/2018 | Balasubramanian et al. | |
| 2018/0337872 A1 | 11/2018 | Fawcett | |
| 2019/0073197 A1 | 3/2019 | Collins | |
| 2019/0089903 A1 | 3/2019 | Debates et al. | |
| 2019/0102064 A1 | 4/2019 | Brown et al. | |
| 2019/0108578 A1 | 4/2019 | Spivack et al. | |
| 2019/0132264 A1 | 5/2019 | Jafar Ali et al. | |
| 2019/0138600 A1 | 5/2019 | Krishnan et al. | |
| 2019/0147098 A1 | 5/2019 | Beller et al. | |
| 2019/0166069 A1 | 5/2019 | Yao et al. | |
| 2019/0172242 A1 | 6/2019 | Bullivant et al. | |
| 2019/0187961 A1 | 6/2019 | Myung et al. | |
| 2019/0206401 A1* | 7/2019 | Liu ....................... G06V 40/174 | |
| 2019/0206407 A1* | 7/2019 | Shukla ................... G10L 15/24 | |
| 2019/0236459 A1 | 8/2019 | Cheyer et al. | |
| 2019/0244407 A1 | 8/2019 | Wiesel et al. | |
| 2019/0251165 A1 | 8/2019 | Bachrach et al. | |
| 2019/0266280 A1 | 8/2019 | Acampado | |
| 2019/0287537 A1 | 9/2019 | Hirzel et al. | |
| 2019/0311036 A1 | 10/2019 | Shanmugam et al. | |
| 2019/0354358 A1 | 11/2019 | Nelson et al. | |
| 2019/0369748 A1 | 12/2019 | Hindi et al. | |
| 2019/0377619 A1 | 12/2019 | Riva et al. | |
| 2019/0378505 A1* | 12/2019 | Wang ..................... G10L 15/22 | |
| 2020/0028885 A1 | 1/2020 | Gordon et al. | |
| 2020/0039080 A1 | 2/2020 | Oyaizu | |
| 2020/0110577 A1 | 4/2020 | Rodgers | |
| 2020/0142719 A1 | 5/2020 | Akbulut et al. | |
| 2020/0197818 A1 | 6/2020 | Ma et al. | |
| 2020/0252353 A1 | 8/2020 | Lalji et al. | |
| 2020/0279658 A1 | 9/2020 | Rao et al. | |
| 2020/0321086 A1 | 10/2020 | Rao et al. | |
| 2020/0394268 A1 | 12/2020 | Ickman et al. | |

* cited by examiner

1000

```
┌─────────────────────────────────────────────────────────────┐
│  RECEIVE, FROM A COMPUTING DEVICE, DATA IDENTIFYING A       │
│                       DETECTED OBJECT                        │
│                            1002                              │
└─────────────────────────────────────────────────────────────┘
                              │
                              ▼
┌─────────────────────────────────────────────────────────────┐
│  BASED ON THE RECEIVED DATA IDENTIFYING THE DETECTED OBJECT,│
│  DETERMINE INFORMATION ASSOCIATED WITH THE DETECTED OBJECT   │
│                            1004                              │
└─────────────────────────────────────────────────────────────┘
                              │
                              ▼
┌─────────────────────────────────────────────────────────────┐
│  CAUSE THE COMPUTING DEVICE TO PRESENT A VIEW OF A GIVEN TYPE│
│  OF VISUAL CONVERSATION APPLICATION THAT ENABLES A SECOND   │
│  USER TO INTERACT WITH A DIGITAL CONVERSATIONAL CHARACTER IN │
│          AN INTERACTIVE CONVERSATIONAL SESSION               │
│                            1006                              │
└─────────────────────────────────────────────────────────────┘
                              │
                              ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│       DETERMINE AN INTERACTION MODE FOR AN INTERACTIVE      │
│  CONVERSATIONAL SESSION BETWEEN THE SECOND USER AND A DIGITAL│
│                   CONVERSATIONAL CHARACTER                   │
│                            1008                              │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                              │
                              ▼
┌─────────────────────────────────────────────────────────────┐
│  FACILITATE THE INTERACTIVE CONVERSATIONAL SESSION BETWEEN  │
│  THE SECOND USER AND THE DIGITAL CONVERSATIONAL CHARACTER    │
│                            1010                              │
└─────────────────────────────────────────────────────────────┘
                              │
                              ▼
┌─────────────────────────────────────────────────────────────┐
│  RECEIVE, FROM THE COMPUTING DEVICE, CONVERSATIONAL DATA     │
│  CORRESPONDING TO INTERACTIONS BETWEEN THE SECOND USER AND   │
│          THE DIGITAL CONVERSATIONAL CHARACTER                │
│                            1012                              │
└─────────────────────────────────────────────────────────────┘
                              │
                              ▼
┌─────────────────────────────────────────────────────────────┐
│           STORE THE RECEIVED CONVERSATIONAL DATA             │
│                            1014                              │
└─────────────────────────────────────────────────────────────┘
```

FIG. 10

Pharmacy name and address

Prescription number

Who the prescription is for

Directions for taking the drug

Quantity in the container

Brand name of the drug

Refills left

1200

CENTRAL PHARMACY
45 Main St, Anytown, US 12345    (800) 555-5555

Rx# 231-479-161            Dr. Jones, John C
SMITH, JANE                DATE 06/24/10
TAKE ONE TABLET ORALLY DAILY OR
EVERY SIX TO EIGHT HOURS AS NEEDED
FOR SYMPTOMS.
24    FAZACLO            TAB 10-500MG
NO REFILLS  CLOZAPINE    USE BEFORE 06/24/12

Doctor who wrote the prescription

Date the prescription was filled

Phone number of the pharmacy

Generic name of the drug

Safety reminders

Dose, or strength, of the drug

Expiration date of the drug

FIG. 12

COMPUTER DEVICE AND METHOD FOR FACILITATING AN INTERACTIVE CONVERSATIONAL SESSION WITH A DIGITAL CONVERSATIONAL CHARACTER

CROSS-REFERENCE TO RELATED APPLICATIONS

This application claims priority to U.S. Non-Provisional application Ser. No. 16/599,439, filed on Oct. 11, 2019, and entitled "Computer System and Method for Facilitating an Interactive Conversational Session with a Digital Conversational Character," which in turn claims priority to (i) U.S. Provisional App. No. 62/828,954, filed Apr. 3, 2019, and entitled "Systems and Methods for Authoring and Managing Conversations," (ii) U.S. Provisional App. No. 62/902,067, filed Sep. 18, 2019, and entitled "Computer System and Method for Content Authoring of a Digital Conversational Character, each of which is incorporated herein by reference in its entirety.

BACKGROUND

Accurate, effective, and personal communication is important in many professional settings, including healthcare and legal, among other industries. Indeed, most industries generally require interactions with various clients, employees, and the like. For instance, a doctor may interact with a patient, a lawyer may interact with a client, or corporate recruiter may interact with a potential candidate. Such individuals may interact with one another using various forms of communication, which may include written communication (e.g., emails, instant messages, text messages, etc.), verbal communication, and/or nonverbal communication (e.g., body language).

In some situations, interactions between certain individuals can be time consuming and can often be repetitive. For instance, patient consultations can be time consuming for a doctor and may generally involve similar conversations with different patients that are often repeated over the course of several patient consultations. For example, a doctor may ask each patient a similar set of questions during a respective patient consultation, and during a given patient consultation, the doctor may encounter questions from a patient that may have been asked by other patients during other patient consultations. Interactions that takes place in other settings (e.g., a job interview) may suffer from similar issues.

Overview

In view of the foregoing, software applications have been developed to facilitate interactions between two individuals (e.g., a customer support agent and a consumer). Some examples of these software applications generally facilitate a chat session between two individuals via instant messaging, where a first individual (e.g., a customer support agent) may ask a second individual (e.g., a consumer) a question during the chat session and the second individual may respond to the question, or vice versa. Some software applications may even enable an individual (e.g., a customer support agent) to interact with multiple individuals (e.g., consumers) in multiple different chat sessions at a given time.

However, while software applications that facilitate a chat session allow individuals to communicate with one another, it is often impersonal and limited to textual and/or voice exchanges. To make the interactions more personal, it often requires the individuals to participate in the chat session, which gives rise to several problems. First, such software applications can be time consuming for professionals (e.g., a doctor, lawyer, businessman, etc.) who may have responsibilities that take precedence over other responsibilities. As a result, a user (e.g., a patient, client, etc.) who has time-sensitive questions may not always be able to get a timely personal response from such professionals, which may be detrimental to the user and the relationship between the user and a given professional.

Second, because such software applications may still require the participation of individuals to facilitate a chat session, they do not resolve the issue involving a given professional (e.g., a doctor) engaging in similar conversations with various users (e.g., patients, clients, etc.) that are often repeated over the course of several different chat sessions.

Third, such software applications typically rely exclusively on non-personal interactions (e.g., written communications), and thus may be less engaging compared to personal interactions with sentiment that go beyond written communications. Further, in some instances, non-personal interactions can be taken out of context without the proper tone, expression, and/or body language behind the interactions. Thus, non-personal interactions that take place during a chat session may not be the most effective means of clearly, accurately, and honestly conveying a message.

Fourth, such software applications typically have limited ways in which an individual can initiate a chat session to interact with another individual. Indeed, most existing software applications require individuals who wish to participate in a chat session to access a front-end software component of their respective computing devices and log into their respective accounts in order to start a chat session between the individuals, which can be inconvenient in some circumstances.

In an effort address some of the forgoing deficiencies, some have developed software applications that facilitate an automated chat session between a chatbot and an individual. However, such software applications still give rise to some of the same problems mentioned above (e.g., reliance on non-personal interactions, limited ways to initiate a chat session, etc.), along with various other problems. For example, creating a chatbot that can facilitate an automated chat session with an individual can be time consuming and generally requires some knowledge and expertise in a programming language. As a result, software applications that facilitate an automated chat session are typically developed by programmers, which can be costly and inefficient for professionals (e.g., a doctor, lawyer, etc.) who may wish to develop an automated chat session tailored for their profession.

Furthermore, because such software applications are typically developed by programmers who may have limited knowledge of a given profession (e.g., medical), a chatbot created for the given profession may be limited to responding to only frequently asked questions during an automated chat session that may not be relevant to individuals who have specific questions regarding an area of practice of the given profession. While a chatbot could be programmed to respond to more than just frequently asked questions, such an effort would require programmers to collaborate with other professionals (e.g., a doctor, lawyer, etc.), and thus can be time consuming and even more costly to develop.

To address one or more of the foregoing deficiencies with existing technology, disclosed herein is a software technology for facilitating an interactive conversational session between a user (e.g., a client, a patient, etc.) and a digital conversational character. At a high level, the disclosed software technology enables a first user (e.g., a professional, such as doctor, lawyer, etc.) to create and employ a digital conversational character that is configured to interact with a second user (e.g., a client, a patient, etc.) during an interactive conversation session. For instance, a digital conversational character created by a doctor may be configured to ask and respond to targeted questions during an interactive conversational session between a patient and the digital conversational character without the need for the doctor to participate in the interactive conversational session.

In one aspect, the disclosed software technology may include a content authoring tool for creating a given type of visual conversation application with one or more digital conversational characters. In one implementation, a first user (e.g., a professional such as a doctor, lawyer, etc.) may access the content authoring tool via the first user's computing device (e.g., computing device 112 of FIG. 1) to create a given type of visual conversation application, which may involve defining conversational content for a digital conversational character that can ask and/or respond to questions from a second user (e.g. a client, a patient, etc.). The given type of visual conversation application created by the first user may be later accessed by the second user via the second user's computing device (e.g., computing device 114 of FIG. 1) to interact with the digital conversational character in an interactive conversational session.

In practice, the content authoring tool may be provided to a party (e.g., an organization) in the form of a software as a service ("SaaS") that includes various other tools (e.g., administrative tools, etc.), in which case the content authoring tool may include a front-end software component running on a first user's computing device (e.g., a professional's computing device) and a back-end software component running on a back-end platform (e.g., back-end platform 102 of FIG. 1) that is accessible to the first user's computing device via a communication network such as the Internet. Further, in practice, the back-end platform associated with the content authoring tool may be capable of serving multiple different parties that have signed up for access to the content authoring tool, where each such party (e.g., each organization) has its own respective account for the content authoring tool and respective users (e.g., professionals) who may have access to the content authoring tool under the respective account. Further yet, in practice, a given type of visual conversation application created by a first user via the content authoring tool may be later accessed by a second user who has permission to access the given type of visual conversation application, in which case the given type of visual conversation application may include a front-end software component running on the second user's computing device and a back-end software component running on a back-end platform that is accessible to the second user's computing device via a communication network such as the Internet.

Generally speaking, a given type of visual conversation application created by a first user using the disclosed content authoring tool may take various forms, examples of which may include a medical conversation application, an interview conversation application, a product conversation application, a training conversation application, and/or a companion conversation application, each of which is described in more detail below.

A digital conversational character that may be created and employed to interact with a second user (e.g., a patient, a client, etc.) during an interactive conversational session may take various forms as well, examples of which may include a digital representation of a human, an animal, a stuffed animal, or a robot, as some non-limiting examples.

In accordance with the present disclosure, the disclosed software technology for facilitating an interactive conversational session between a second user (e.g., a client, a patient, etc.) and a digital conversational character may involve two primary phases: (1) a first phase (which may be referred to herein as the "authoring phase") that involves a first user accessing the disclosed content authoring tool to create a given type of visual conversation application that facilitates interactions between a second user and a digital conversational character in an interactive conversational session, and (2) a second phase (which may be referred to herein as the "rendering phase") that involves the second user accessing the created visual conversation application to interact with the digital conversational character in an interactive conversational session. Each of these phases—which may take various forms and be carried out in various manners—are described in further detail below.

In one example implementation, the authoring phase of the disclosed process may involve (1) causing a first computing device to present a view of a content authoring tool that enables a first user to create a visual conversational application, (2) receiving data from the first computing device to create a given type of visual conversation application, (3) generating a set of conversational content that may be used to define conversational content for a digital conversational character, (4) receiving, from the first computing device, data that defines the digital conversational character, and (5) based on the received data, creating the given type of visual conversation application. These functions are described in further detail below.

In turn, the rendering phase of the disclosed process may involve (1) receiving, from a second computing device, data identifying a detected object, (2) based on the received data, determining information associated with the detected object, (3) causing the second computing device to present a view of a given type of visual conversation application created in the authoring phase that enables a second user to interact with a digital conversational character in an interactive conversational session, (4) optionally determining an interaction mode for an interactive conversational session between the second user and a digital conversational character, (5) facilitating the interactive conversational session between the second user and the digital conversational character, (4) receiving, from the computing device, conversational data corresponding to interactions between the second user and the digital conversational character, and (5) storing the received conversational data. These functions are described in further detail below.

Accordingly, in one aspect, disclosed here is a method performed by a computing system that involves (1) receiving, from a computing device associated with a user, data identifying an object that has been detected, (2) based on the received data identifying the detected object, determining information associated with the detected object, (3) causing the computing device associated with the user to present a view of a given type of visual conversation application that enables the user to interact with a digital conversational character in an interactive conversational session, (4) determining a given interaction mode from a plurality of interaction modes for the interactive conversational session between the user and the digital conversational character, wherein the plurality of interaction modes comprises a personal mode and a non-personal mode, and (5) facilitating the interactive conversational session between the user and the digital conversational character based on the determined information associated with the detected object and the determined interaction mode.

In another aspect, disclosed herein is a computing system that includes a network interface, at least one processor, a non-transitory computer-readable medium, and program instructions stored on the non-transitory computer-readable medium that are executable by the at least one processor to cause the computing system to carry out the functions disclosed herein, including but not limited to the functions of the foregoing method.

In yet another aspect, disclosed herein is a non-transitory computer-readable storage medium provisioned with software that is executable to cause a computing system to carry out the functions disclosed herein, including but not limited to the functions of the foregoing method.

One of ordinary skill in the art will appreciate these as well as numerous other aspects in reading the following disclosure.

BRIEF DESCRIPTION OF THE DRAWINGS

FIG. 10 depicts another example flow chart for the rendering phase of the present disclosure.

FIG. 12 depicts an example prescription label in accordance with the present disclosure.

DETAILED DESCRIPTION

The following disclosure makes reference to the accompanying figures and several example embodiments. One of ordinary skill in the art should understand that such references are for the purpose of explanation only and are therefore not meant to be limiting. Part or all of the disclosed systems, devices, and methods may be rearranged, combined, added to, and/or removed in a variety of manners, each of which is contemplated herein.

I. EXAMPLE SYSTEM CONFIGURATION

As described above, the present disclosure is generally directed to software technology for facilitating an interactive conversational session between a user (e.g., a client, a patient, etc.) and a digital conversational character. At a high level, the disclosed software technology enables a first user (e.g., a professional such as a doctor, lawyer, etc.) to create and employ a digital conversational character that is configured to interact with a second user (e.g., a client, a patient, etc.) during an interactive conversational session. For instance, a digital conversational character created by a doctor may be configured to ask and respond to targeted questions during an interactive conversational session between a patient and the digital conversational character without the need for the doctor to participate in the interactive conversational session.

Figure 1:
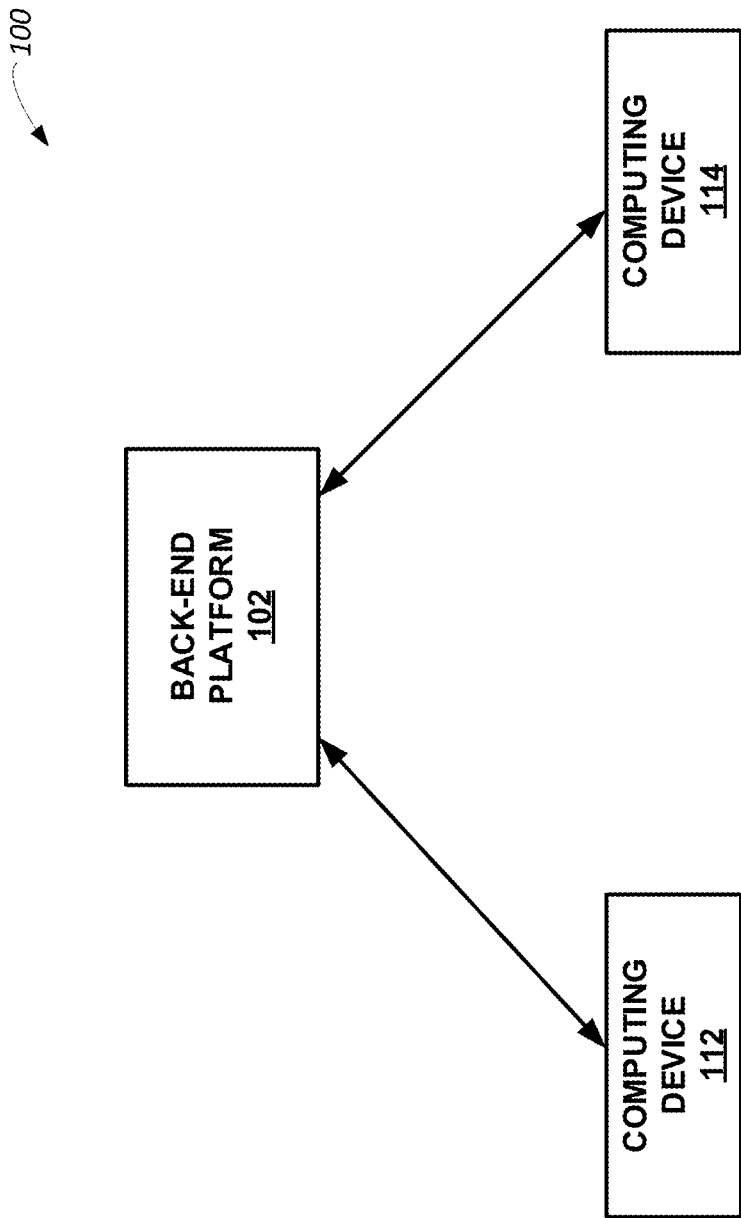
FIG. 1 depicts an example network configuration in which example embodiments may be implemented.

Turning now to the figures, FIG. 1 depicts an example system configuration 100 in which example embodiments of the present disclosure may be implemented. As shown in FIG. 1, system configuration 100 includes a back-end platform 102 that may be communicatively coupled to one or more computing devices, such as computing device 112, 114.

In general, back-end platform 102 may comprise one or more computing systems that have been provisioned with software for carrying out one or more of the platform functions disclosed herein for driving a content authoring software application and/or a visual conversation application created via the content authoring software application. The one or more computing systems of back-end platform 102 may take various forms and be arranged in various manners.

For instance, as one possibility, back-end platform 102 may comprise computing infrastructure of a public, private, and/or hybrid cloud-based system (e.g., computing and/or storage clusters) that has been provisioned with software for carrying out one or more of the platform functions disclosed herein. In this respect, the entity that owns and operates back-end platform 102 may either supply its own cloud infrastructure or may obtain the cloud infrastructure from a third-party provider of "on demand" computing resources, such as, for example, Amazon Web Services (AWS) or the like. As another possibility, back-end platform 102 may comprise one or more dedicated servers that have been provisioned with software for carrying out one or more of the platform functions disclosed herein.

In practice, back-end platform 102 may be capable of serving multiple different parties (e.g., organizations) that have signed up for access to the content authoring software application, where each such party has its own respective account for the content authoring software application. Further, in practice, a visual conversation application created by a party's user (e.g., a doctor) via the content authoring software application using computing device 112 may be later accessed by a second user (e.g., a patient) who has permission to access the visual conversation application, in which case the visual conversation application may include a front-end software component running on the second user's computing device (e.g., computing device 114) and a back-end software component running on back-end platform 102 that is accessible to the second user's computing device 114 via a communication network such as the Internet.

Further, other implementations of back-end platform 102 are possible as well.

In turn, computing device 112, 114 may take any of various forms, examples of which may include a desktop computer, a laptop, a netbook, a tablet, a smartphone, a smart wearable device (e.g., smart watch, glasses, etc.), a smart TV, and/or a personal digital assistant (PDA), among other possibilities.

As further depicted in FIG. 1, back-end platform 102, computing device 112, and computing device 114 are configured to interact with one another over respective communication paths. Each respective communication path with back-end platform 102 may generally comprise one or more communication networks and/or communications links, which may take any of various forms. For instance, each respective communication path with back-end platform 102 may include any one or more of point-to-point links, Personal Area Networks (PANs), Local-Area Networks (LANs), Wide-Area Networks (WANs) such as the Internet or cellular networks, cloud networks, and/or operational technology (OT) networks, among other possibilities. Further, the communication networks and/or links that make up each respective communication path with back-end platform 102 may be wireless, wired, or some combination thereof, and may carry data according to any of various different communication protocols. Although not shown, the respective communication paths with back-end platform 102 may also include one or more intermediate systems. For example, it is possible that back-end platform 102 may communicate with computing device 112 and/or computing device 114 via one or more intermediary systems, such as a host server (not shown). Many other configurations are also possible.

Similarly, the communication path between computing device 112, 114 may generally comprise one or more communication networks and/or communications links, which may also take various forms. For instance, the communication path between computing device 112, 114 may include any one or more of point-to-point links, Personal Area Networks (PANs), and Local-Area Networks (LANs), among other possibilities. Further, the communication networks and/or links that make up the communication path between computing device 112, 114 may be wireless, wired, or some combination thereof, and may carry data according to any of various different communication protocols. Many other configurations are also possible.

Although not shown in FIG. 1, back-end platform 102 may also be configured to receive data from one or more external data sources that may be used to facilitate functions related to the disclosed process. A given external data source—and the data output by such data sources—may take various forms.

It should be understood that system configuration 100 is one example of a network configuration in which embodiments described herein may be implemented. Numerous other arrangements are possible and contemplated herein. For instance, other network configurations may include additional components not pictured and/or more or less of the pictured components.

In practice, in line with the example configuration above, the disclosed content authoring tool may be running on a computing device of a first user (e.g., computing device 112) who may wish to create a given type of visual conversation application. The given type of visual conversation application created may then be installed and executed on a computing device of a second user (e.g., computing device 114) who may wish to interact with a digital conversational character in an interactive conversational session disclosed in more detail below. One of ordinary skill in the art will appreciate that it may be possible to install and execute the disclosed content authoring tool and the given type of visual conversational application created using the content authoring tool on a single computing device (e.g., computing device 112) or different computing devices (e.g., computing devices 112 and 114).

II. EXAMPLE PLATFORM

Figure 2A:
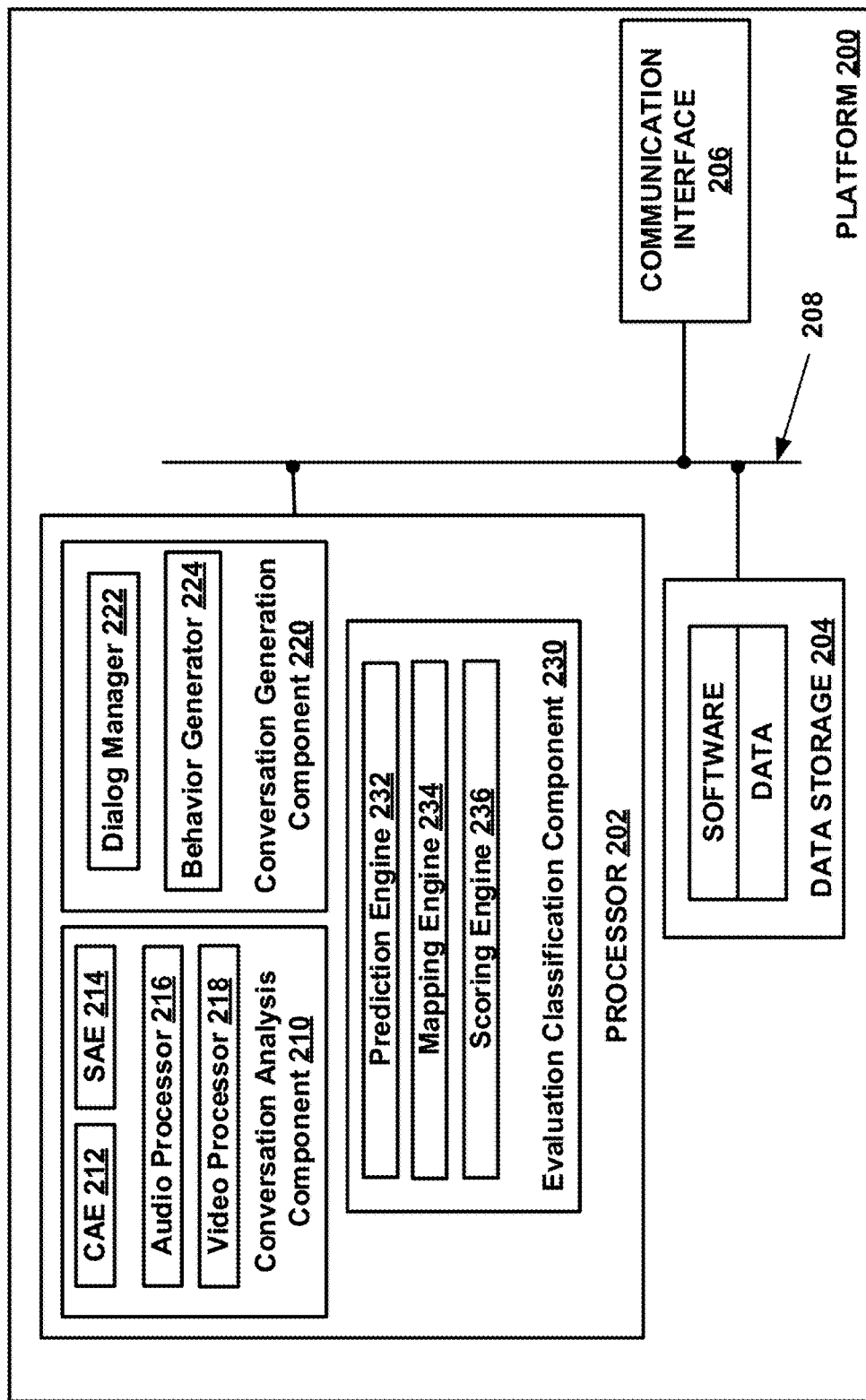
FIG. 2A depicts an example computing platform that may be configured carry out one or more of the functions of the present disclosure.

FIG. 2A is a simplified block diagram illustrating some structural components that may be included in an example computing platform 200, which could serve as back-end platform 102 of FIG. 1. In line with the discussion above, platform 200 may generally comprise one or more computer systems (e.g., one or more servers), and these one or more computer systems may collectively include at least a processor 202, data storage 204, and a communication interface 206, all of which may be communicatively linked by a communication link 208 that may take the form of a system bus, a communication network such as a public, private, or hybrid network, or some other connection mechanism.

Processor 202 may comprise one or more processor components, such as general-purpose processors (e.g., a single- or multi-core microprocessor), special-purpose processors (e.g., an application-specific integrated circuit or digital-signal processor), programmable logic devices (e.g., a field programmable gate array), controllers (e.g., microcontrollers), and/or any other processor components now known or later developed. In line with the discussion above, it should also be understood that processor 202 could comprise processing components that are distributed across a plurality of physical computing devices connected via a network, such as a computing cluster of a public, private, or hybrid networks.

In one implementation, as shown in FIG. 2A, processor 202 may comprise a conversation analysis component 210, a conversation generation component 220, and an evaluation classification component 230. Generally speaking, conversation analysis component 210 may be configured to analyze and interpret inputs received from a user's computing device (e.g., computing device 112, 114 of FIG. 1). For instance, conversation analysis component 210 may be configured to analyze audio and/or video data of a user's (e.g., a patient's) responses to capture a variety of information including answers to questions, personality traits, knowledge levels, skills, body language, and/or stress levels, among other examples. Conversation analysis component 210 may take various forms.

As one possibility, conversation analysis component 210 may include content analysis engine ("CAE") 212, sentiment analysis engine ("SAE") 214, audio processor 216, and video processor 218. CAE 212 may be configured to analyze processed audio and/or video data to interpret a user's response. In some instances, various natural language processing (NLP) methods may be used to capture a user's spoken response and parse the user's response to identify key words that can be used to interpret and/or score the user's response.

SAE 214 may be configured to analyze processed audio and/or video data to capture additional information about a user, beyond the literal meaning of responses provided by the user, such as the user's sentiment. For example, in some implementations, a user's voice fluctuations, tone, pauses, use of filler words, and/or use of corrective statements can be used to identify levels of stress or discomfort. In some implementations, SAE 214 may be configured to analyze video data (or features identified from the video data) to determine various characteristics or observations about a user, examples of which may include a user's comfort level, personality trait, mood, ability to make eye contact, stress level, emotional state, and/or expressiveness, among other examples.

In some instances, analyzed sentiments can be used in real-time to affect the behavior of a digital conversational character in a variety of ways. For instance, based on an analyzed sentiment, a digital conversational character may become more or less chatty, more or less friendly, and/or more or less expressive. The changes in the behavior of a digital conversational character can then be used to further analyze a user's response to the changing behavior.

Audio processor 216 may be configured to process audio data from an interactive conversational session between a user and a digital conversational character. For instance, audio processor 216 may be configured to process audio data corresponding to a user's utterance during an interactive conversational session. In some implementations, audio processor 216 may be configured to analyze the ambient background noise against a user's utterance in order to isolate the background noise and parse the beginning of the user's utterance as well as the end of the user's utterance. In other implementations, audio processor 216 may be configured to use various continuous speech recognition techniques known in the art to parse the beginning and the end of a user's utterance.

Further, in some implementations, audio processor 216 may employ various methods to convert the audio data into an interpretable form, such as Automatic Speech Recognition (ASR). In other implementations, audio processor 216 may use a speech to text (STT) process to produce textual outputs that can be further processed to capture meaning, emotions, sentiment, and/or stress levels. In some instances, audio processor 216 may apply filters to the audio data (and/or to textual outputs generated from the audio data) to edit unnecessary elements, such as pauses, filler words, and/or corrected statements. Further, in some implementations, these elements can be used as an additional metric to capture metadata related to a user's conversational skills to support the capture of a variety of information including (but not limited to) answers to questions, personality traits, knowledge levels, skills, body language, and/or stress levels.

Video processor 218 may be configured to process video data from an interactive conversational session between a user and a digital conversational character. In some implementations, video processor 218 may be used to analyze video for visual cues that may not be readily apparent in the audio data captured during an interactive conversational session, such as a user's body language. In some instances, video processor 218 may employ various machine learning methods, such as convolutional neural networks, recurrent neural networks, and/or capsule networks, to analyze video segments and/or captured images to identify features that can be used to analyze a user's body language.

One of ordinary skill in the art will appreciate that conversation analysis component 210 may take various other forms and may include various other elements as well.

In accordance with the present disclosure, conversation generation component 220 may be configured to generate a script for a digital conversational character. The script can be generated based on a variety of different factors, such as information about a user involved in an interactive conversational session with the digital conversational character. In several implementations, the script may be generated dynamically, adjusting with each response received from a user during an interactive conversational session, based on the content, sentiment, and/or other factors identified from the user's response. In certain implementations, a first user (e.g., a doctor) may manually author a script that is used during an interactive conversational session between a digital conversational character and a second user (e.g., a patient), which in some instances may involve fine-tuning existing content to convey information in a certain way, including (but not limited to) a positive or negative disposition of the digital conversational character, emphasis of a certain word or phrase, etc. In this respect, conversation generation component 220 may take various forms.

As one example, conversation generation component 220 may include dialog manager 222 and behavior generator 224. Dialog manager 222 may be configured to generate dialog that is to be presented to a user. For instance, dialog manager 222 may be configured to generate a textual script that can be provided in audio or text form at a user's computing device 112 and/or computing device 114. In some implementations, the script may be selected from a set of predefined scripts. In other implementations, the script may be generated dynamically using machine learning methods including, but not limited to, generative adversarial networks (GANs), recurrent neural networks (RNNs), capsule networks, and/or restricted Boltzmann machines (RBMs).

Behavior generator 224 may be configured to generate behaviors for a digital conversational character that converses with a user during an interactive conversational session. For instance, behavior generator 224 may be configured to generate randomized behaviors and gestures to create a sense of realism during an interactive conversational session with a user. In some implementations, such behaviors may be generated based on machine learning methods, such as generative adversarial networks (GANs) and/or Restricted Boltzmann Machines (RBMs). In other implementations, behaviors may be generated in a standardized format for describing model animations, such as Behavioral Markup Language (BML).

In some embodiments, behavior generator 224 may receive information about a user as input to the behavior generation. In certain embodiments, behaviors for a digital conversational character may be generated to mimic the body language of a user to put the user at ease or to develop a sense of rapport. For instance, behavior generator 224 may provide movements and postures to indicate that the digital conversational character is listening, waiting for further clarification, processing user input, or (temporarily) disengaged from the conversation with user. In some embodiments, behavior generators can identify facial expressions to indicate emotions, such as confusion, agreement, anger, happiness, and disappointment. In a variety of embodiments, behavior generator 224 may be configured to generate customized behaviors for a digital conversational character, which may be based on a variety of factors, such as character, personality archetype, and/or culture. In some instances, behavior generator 224 may be configured to generate customized behaviors for a digital conversational character based on behavior of a first user during the authoring phase that the first user may act in (described in more detail below), which may be interpreted, for example, by audio processor 216 and/or video processor 218.

One of ordinary skill in the art will appreciate that conversation generation component 220 may take various other forms and may include various other elements as well.

Evaluation classification component 230 may take various forms as well. In general, evaluation classification component 230 may be configured to evaluate an interactive conversational session between a user and a digital conversational character (or the user involved in the interactive conversational session). For instance, evaluation classification component 230 may be configured to evaluate a user's response time to a question, a user's stress level, knowledge, and/or competency. The evaluation may be performed during an interactive conversational session between a user and a digital conversational character and/or after the interactive conversational session has ended.

In some implementations, the evaluations of an interactive conversational session between a user and a digital conversational character (or the user involved in the interactive conversational session) can be used to train a model to adjust future interactive conversational sessions. Adjustments for the future interactive conversational sessions may include changing the digital conversational character's behaviors, reactions, gestures, and questions that are generated in response to interactions with a user. In implementations where an interactive conversational session involves a user and multiple digital conversational characters, each digital conversational character may exhibit certain behaviors as described herein which may change over time.

As shown in FIG. 2A, evaluation classification component 230 may include prediction engine 232, mapping engine 234, and scoring engine 236. Prediction engine 232 may be configured to make predictions about a user involved in an interactive conversational session with a digital conversational character, such as the user's stress level, knowledge, and/or competency.

Scoring engine 236 may be configured to generate scores for a user involved in an interactive conversational session with a digital conversational character that can be used to summarize various aspects of the user, such as the user's personality traits, technical skills, knowledge, and/or soft skills. In some implementations, scoring engines can also include various statistics related to an interactive conversational session, including a user's response time, length of sentences, and/or vocabulary diversity.

Although scoring engine 236 is described as part of platform 200, in some implementations, scoring engine 236 may be provided by a third party system that analyzes various characteristics provided by platform 200 to generate a score. For example, in some cases, a third party system may be used to generate personality scores and/or technical competence scores based on text of a user's answers to specific questions during an interactive conversational session with a digital conversational character.

Mapping engine 234 may be configured to identify scores for individual characteristics of a user and map them to criteria to be reported for an interactive conversational session. For example, a score for friendliness of a user, which may be generated by scoring engine 236 based on various factors (e.g., smiling, voice tone, language, and eye contact, etc.), may be mapped to a criteria to report the level of friendliness of the user involved in an interactive conversational session with a digital conversational character.

One of ordinary skill in the art will appreciate that evaluation classification component 230 may take various other forms and may include various other elements as well. Further, one of ordinary skill in the art will appreciate that processor 202 may comprise other processor components as well.

As further shown in FIG. 2. Platform 200 may also include data storage 204 that comprise one or more non-transitory computer-readable storage mediums, examples of which may include volatile storage mediums such as random-access memory (RAM), registers, cache, etc. and non-volatile storage mediums such as read-only memory (ROM), a hard-disk drive, a solid-state drive, flash memory, an optical-storage device, etc. In line with the discussion above, it should also be understood that data storage 204 may comprise computer-readable storage mediums that are distributed across a plurality of physical computing devices connected via a network, such as a storage cluster of a public, private, or hybrid cloud-based storage systems.

As shown, data storage 204 may be provisioned with software components that enable the platform 200 to carry out the platform-side functions disclosed herein. These software components may generally take the form of program instructions that are executable by the processor 202 to carry out the disclosed functions, which may be arranged together into software applications, virtual machines, software development kits, toolsets, or the like. Further, data storage 204 may be arranged to store data in one or more databases, file systems, or the like. Data storage 204 may take other forms and/or store data in other manners as well.

Communication interface 206 may be configured to facilitate wireless and/or wired communication with external data sources and or computing devices, such as computing device 112, 114 in FIG. 1. Additionally, in an implementation where platform 200 comprises a plurality of physical computing devices connected via a network, communication interface 206 may be configured to facilitate wireless and/or wired communication between these physical computing devices (e.g., between computing and storage clusters in a cloud network). As such, communication interface 206 may take any suitable form for carrying out these functions, examples of which may include an Ethernet interface, a serial bus interface (e.g., Firewire, USB 3.0, etc.), a chipset and antenna adapted to facilitate wireless communication, and/or any other interface that provides for wireless and/or wired communication. Communication interface 206 may also include multiple communication interfaces of different types. Other configurations are possible as well.

Although not shown, platform 200 may additionally include one or more interfaces that provide connectivity with external user-interface equipment (sometimes referred to as "peripherals"), such as a keyboard, a mouse or trackpad, a display screen, a touch-sensitive interface, a stylus, a virtual-reality headset, speakers, etc., which may allow for direct user interaction with platform 200.

It should be understood that platform 200 is one example of a computing platform that may be used with the embodiments described herein. Numerous other arrangements are possible and contemplated herein. For instance, other computing platforms may include additional components not pictured and/or more or less of the pictured components.

III. EXAMPLE COMPUTING DEVICE

Figure 2B:
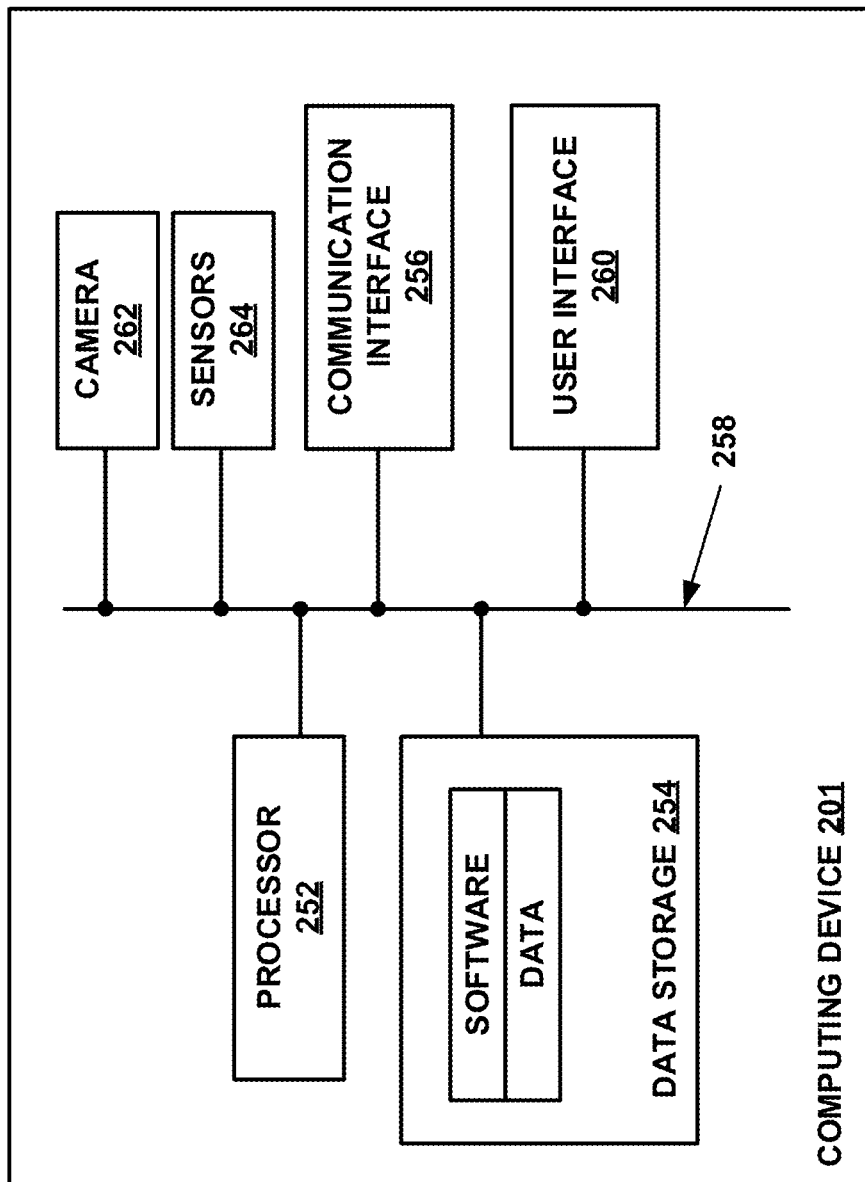
FIG. 2B depicts an example computing device that may be configured to carry out one or more of the functions of the present disclosure.

FIG. 2B is a simplified block diagram illustrating some structural components that may be included in an example computing device 201, which could serve as computing device 112 and/or computing device 114 of FIG. 1.

Computing device 201 may generally comprise a processor 252, data storage 254, communication interface 256, user interface 260, camera 262, and sensors 264, all of which may be communicatively linked by a communication link 258 that may take the form of a system bus or some other connection mechanism. In line with the discussion above, computing device 201 may take various forms, examples of which may include a wearable device, a laptop, a netbook, a tablet, and/or a smartphone, among other possibilities.

Processor 252 may comprise one or more processor components, such as general-purpose processors (e.g., a single- or multi-core microprocessor), special-purpose processors (e.g., an application-specific integrated circuit or digital-signal processor), programmable logic devices (e.g., a field programmable gate array), controllers (e.g., microcontrollers), and/or any other processor components now known or later developed.

In turn, data storage 254 may comprise one or more non-transitory computer-readable storage mediums, examples of which may include volatile storage mediums such as random-access memory (RAM), registers, cache, etc. and non-volatile storage mediums such as read-only memory (ROM), a hard-disk drive, a solid-state drive, flash memory, an optical-storage device, etc.

As shown in FIG. 2B, data storage 254 may be provisioned with software components that enable computing device 201 to carry out authoring and/or rendering functions disclosed herein. In some embodiments, data storage 254 may be provisioned with software components that enable computing device 201 to carry out functions to present a view of the real-world environment that has overlaid virtual content. In this respect, computing device 201 may be a computing device with augmented reality ("AR") capabilities that can be used to present an enhanced view that superimposes virtual content on a view of the real-world environment.

Generally speaking, the software components described above may generally take the form of program instructions that are executable by processor 252 to carry out the disclosed functions, which may be arranged together into software applications, virtual machines, software development kits, toolsets, or the like. Further, data storage 254 may be arranged to store data in one or more databases, file systems, or the like. Data storage 254 may take other forms and/or store data in other manners as well.

Communication interface 256 may be configured to facilitate wireless and/or wired communication with another network-enabled system or device, such as back-end platform 102 or computing device 112, 114. Communication interface 256 may take any suitable form, examples of which may include an Ethernet interface, a serial bus interface (e.g., Firewire, USB 3.0, etc.), a chipset and antenna adapted to facilitate wireless communication, and/or any other interface that provides for wireless and/or wired communication. Communication interface 256 may also include multiple communication interfaces of different types. Other configurations are possible as well.

User interface 260 may be configured to facilitate user interaction with computing device 201 and may also be configured to facilitate causing computing device 201 to perform an operation in response to user interaction. Examples of user interface 260 include a touch-sensitive interface, mechanical interface (e.g., levers, buttons, wheels, dials, keyboards, etc.), and other input interfaces (e.g., microphones), among other examples. In some cases, user interface 260 may include or provide connectivity to output components, such as display screens, speakers, headphone jacks, and the like.

Camera 262 may be configured to capture a real-world environment in the form of image data and may take various forms. As one example, camera 262 may be forward-facing to capture at least a portion of the real-world environment perceived by a user. One of ordinary skill in the art will appreciate that camera 262 may take various other forms as well.

Sensors 264 may be generally configured to capture various data. As one example, sensors 264 may comprise a microphone capable of detecting sound signals and converting them into electrical signals that can be captured via computing device 201. As another examples, sensors 264 may comprise sensors (e.g., accelerometer, gyroscope, and/or GPS, etc.) capable of capturing a position and/or orientation of computing device 201, and such sensor data may be used to determine the position and/or orientation of computing device 201.

Although not shown, computing device 201 may additionally include one or more interfaces that provide connectivity with external user-interface equipment (sometimes referred to as "peripherals"), such as a keyboard, a mouse or trackpad, a display screen, a touch-sensitive interface, a stylus, speakers, etc., which may allow for direct user interaction with AR-enabled computing device 201.

It should be understood that computing device 201 is one example of a computing device that may be used with the embodiments described herein. Numerous other arrangements are possible and contemplated herein. For instance, other computing devices may include additional components not pictured and/or more or less of the pictured components.

IV. EXAMPLE OPERATIONS

As described above, the present disclosure is generally directed to software technology for facilitating an interactive conversational session between a user (e.g., a client, a patient, etc.) and a digital conversational character. At a high level, the disclosed software technology enables a first user (e.g., a professional, such as a doctor, lawyer, etc.) to create and employ a digital conversational character that is configured to interact with a second user (e.g., a client, a patient, etc.) during an interactive conversational session.

In one aspect, the disclosed software technology may include a content authoring tool for creating a given type of visual conversation application with one or more digital conversational characters. In one implementation, a first user (e.g., a professional such as a doctor, lawyer, etc.) may access the content authoring tool via the first user's computing device (e.g., computing device 112) to create a given type of visual conversation application, which may involve authoring conversational content for a digital conversational character that can ask and/or respond to questions from a second user (e.g. a client, a patient, etc.). The given type of visual conversation application created by the first user may be later accessed by the second user via the second user's computing device (e.g., computing device 114) to interact with the digital conversational character in an interactive conversational session.

In practice, the content authoring tool may be provided to a party (e.g., an organization) in the form of a software as a service ("SaaS") that includes various other tools (e.g., administrative tools, etc.), in which case the content authoring tool may include a front-end software component running on a first user's computing device 112 (e.g., a professional's computing device) and a back-end software component running on a back-end platform 102 that is accessible to the first user's computing device 112 via a communication network such as the Internet. Further, in practice, the back-end platform 102 associated with the content authoring tool may be capable of serving multiple different parties that have signed up for access to the content authoring tool, where each such party (e.g., each organization) has its own respective account for the content authoring tool and respective users (e.g., professionals) who may have access to the content authoring tool under the respective account. Further yet, in practice, a given type of visual conversation application created by a first user via the content authoring tool may be later accessed by a second user who has permission to access the given type of visual conversation application, in which case the given type of visual conversation application may include a front-end software component running on the second user's computing device 114 and a back-end software component running on a back-end platform 102 that is accessible to the second user's computing device 114 via a communication network such as the Internet.

Generally speaking, a given type of visual conversation application created by a first user using the disclosed content authoring tool may take various forms. As one example, a given type of visual conversation application, which may be created by a medical professional (e.g., a doctor), may comprise a medical conversation application that generally enables a patient to interact with a digital conversational character during an interactive conversational session regarding a medical matter (e.g., information about a drug, medical procedure, medical condition, etc.). As another example, a given type of visual conversation application, which may be created by a business professional, may comprise an interview conversation application that generally enables an interviewee to interact with a digital conversational character that is configured to interview the interviewee during an interactive conversational session. As yet another example, a given type of visual conversation application may comprise a product conversation application that generally enables a customer to interact with a digital conversational character during an interactive conversational session regarding a product-related matter (e.g., information about a product, product support, etc.). A given type of visual conversation application may take various other forms as well. As still another example, a given type of visual conversation application may comprise a training conversation application that generally enables a trainee for a given job to interact with a digital conversational character that is configured to teach the trainee during an interactive conversational session. As still another example, a given type of visual conversation application may comprise a companion conversation application that generally enables an individual to interact with a digital conversational character that is configured to provide companionship (e.g., by engaging the individual in game-based activities for recreation, engaging the individual in conversations about their day, etc.) during an interactive conversational session. A given type of visual conversation application created by a first user using the disclosed content authoring tool may take various other forms as well.

Figure 3:
FIG. 3 depicts example digital conversational characters in accordance with the present disclosure.

A digital conversational character that may be created and employed to interact with a second user (e.g., a patient, a client, etc.) during an interactive conversational session may take various forms as well. FIG. 3 depicts several illustrative example digital conversational characters that may be created and employed to interact with a second user during an interactive conversational session. As shown, a digital conversational character may take the form of a digital representation of a human (that may be customized to represent a certain profession, race, gender, etc.), an animal (e.g., a guerilla, dog, etc.), a stuffed animal (e.g., a teddy bear), or a robot, as some non-limiting examples. A digital conversational character may take the form of a three-dimensional model or a two-dimensional model.

As another example, a digital conversational character may take the form of a machine (e.g., a robot) that is configured to interact with a second user during an interactive conversational session. In some implementations, the machine may be designed to resemble a human (that may represent a certain profession, race, gender, etc.), an animal (e.g., a guerilla, dog, etc.), or the like.

One of ordinary skill in the art will appreciate that a digital conversational character may take various other forms as well. Further, while a single digital conversational character can be created and employed to interact with a second user (e.g., a patient, a client, etc.) during an interactive conversational session, one of ordinary skill in the art will appreciate that, in some instances, multiple digital conversational characters can be created and employed such that a second user (e.g., a patient, a client, etc.) may interact with multiple digital conversational characters during an interactive conversational session.

For instance, in some implementations, a given digital conversational character for a given type of visual conversation application may be configured with a certain level of expertise. For example, a first digital conversational character for a given type of visual conversation application (e.g. medical conversation application) may be configured to provide more substantive medical responses regarding a specific area of practice (e.g., hand surgery), while a second digital conversational character for the given type of visual conversation application may be configured to provide less substantive medical responses. In this respect, a first user (e.g., doctor, lawyer, professional, etc.) may choose an appropriate digital conversational character for a second user (e.g., patient, client, etc.) to interact with in an interactive conversational session, and the second user may interact with multiple digital conversational characters in an interactive conversational session at the same time or at different times during the interactive conversational session.

In accordance with the present disclosure, the disclosed software technology for facilitating an interactive conversational session between a second user (e.g., a client, a patient, etc.) and a digital conversational character may involve two primary phases: (1) a first phase (which may be referred to herein as the "authoring phase") that involves a first user accessing the disclosed content authoring tool to create a given type of visual conversation application that facilitates interactions between a second user and a digital conversational character in an interactive conversational session, and (2) a second phase (which may be referred to herein as the "rendering phase") that involves the second user accessing the created visual conversation application to interact with the digital conversational character in an interactive conversational session. Each of these phases—which may take various forms and be carried out in various manners—are described in further detail below.

A. Example Authoring Phase

Figure 4:
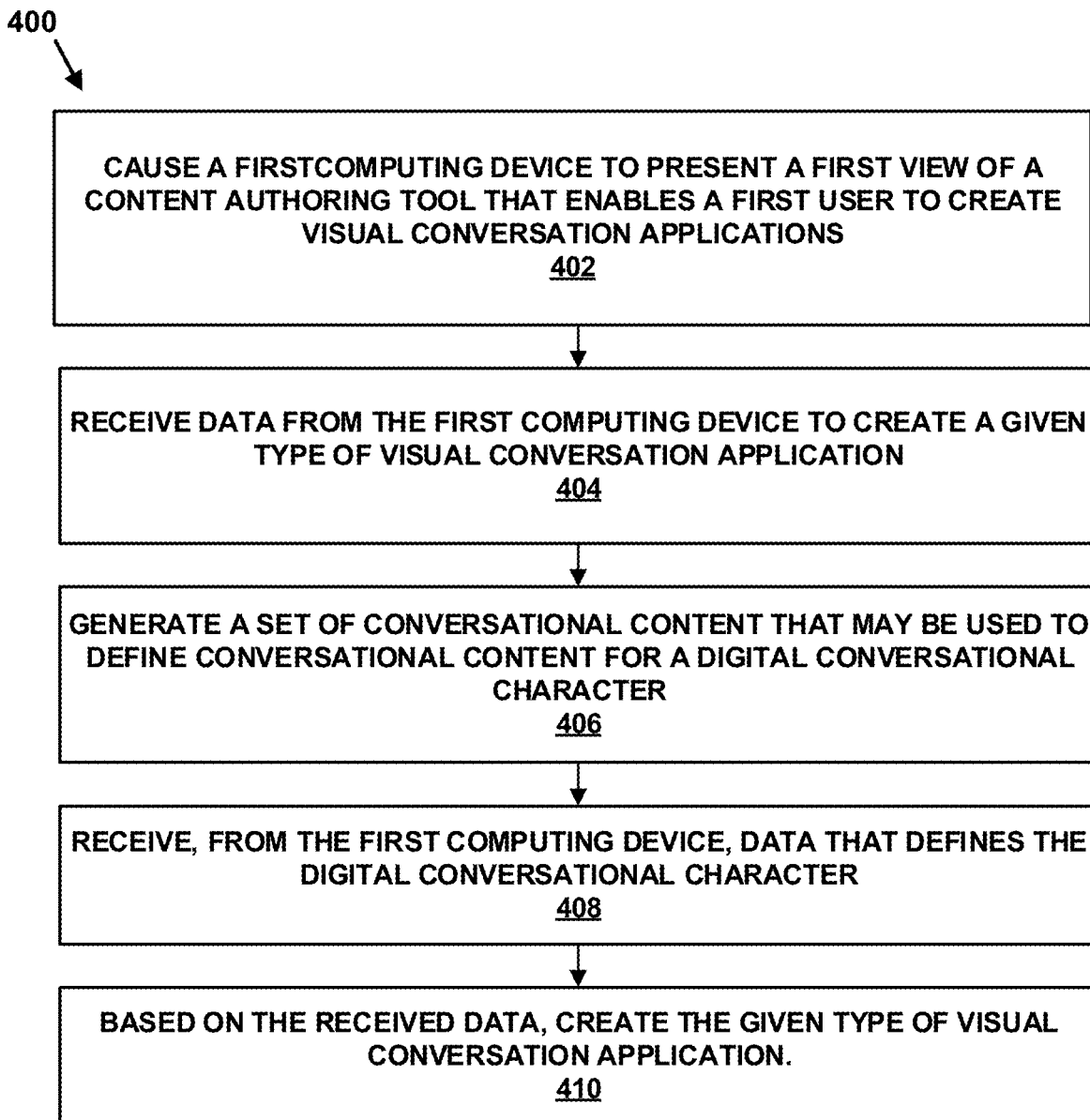
FIG. 4 depicts an example flow chart for the authoring phase of the present disclosure.

Method 400 shown in FIG. 4 presents an embodiment of a method of an authoring phase that can be implemented within an operating environment including or involving, for example, the operating system 100 of FIG. 1, the computing platform 200 of FIG. 2A, and/or the computing device 201 of FIG. 2B. Method 400 may include one or more operations, functions, or actions as illustrated by one or more blocks 402-410. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

According to an example implementation, the authoring phase of the disclosed process may begin with a first user (e.g., a professional, such as a doctor, lawyer, etc.) accessing the disclosed content authoring tool via the first user's computing device (e.g., computing device 112) in order to create one or more visual conversation applications. In practice, the first user may request access to the content authoring tool by, for example, launching a native application on the first user's computing device 112 and logging into the first user's account or directing a web browser on the first user's computing device 112 associated to a uniform resource locator (URL) for the content authoring tool and logging into the first user's account, either of which may cause the first user's computing device 112 to send a request to back-end platform 102 to access the content authoring tool.

At block 402, in response to receiving a request from the first user's computing device 112 to access the content authoring tool, back-end platform 102 may cause the computing device 112 to present a view of the content authoring tool that enables the first user to create visual conversation applications. Back-end platform 102 may also create an instance of the visual conversation application that is associated with the first user. The view of the content authoring tool may take various forms.

Figure 5:
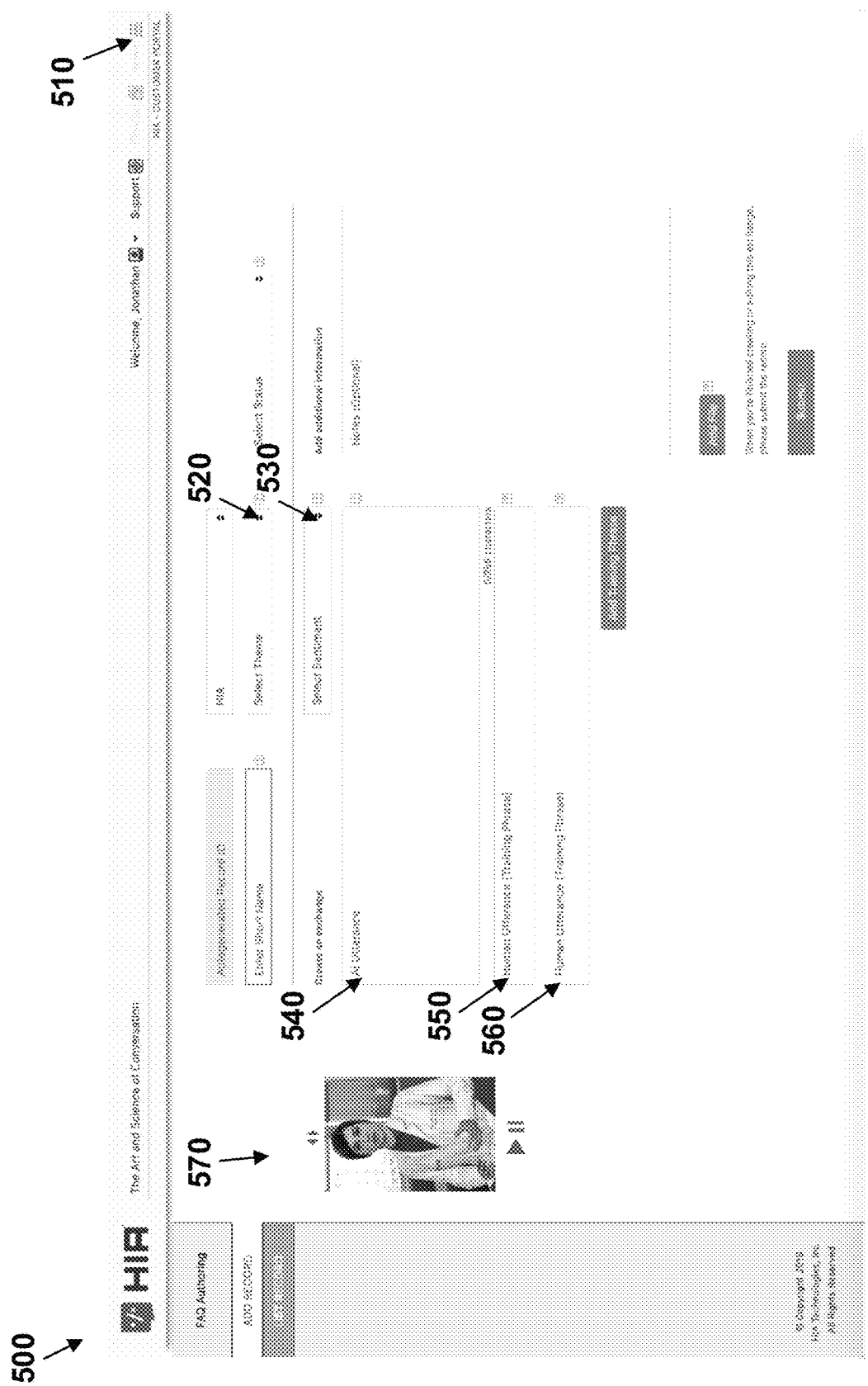
FIG. 5 depicts an example view of the disclosed content authoring tool that may be presented to a computing device.

As one possibility, FIG. 5 depicts an example view 500 of the content authoring tool that includes various elements (e.g., menus, windows, data fields, etc.) that the first user may interact with in order to provide input that is used to create a visual conversational application that employs a digital conversational character. As shown, view 500 presents a view that enables the first user to provide input to create targeted questions and responses for a digital conversational character. In this respect, view 500 includes various elements, such as menu 510, theme data field 520, sentiment data field 530, response data field 540, question data fields 550 and 560, and preview region 570. These elements are described in more detail below.

One of ordinary skill in the art will appreciate that view 500 may include additional elements not shown and/or more or less of the depicted elements. Further, one of ordinary skill in the art will appreciate that the view of the content authoring tool may take various other forms as well.

In turn, the first user may provide input to create a given type of visual conversation application. For instance, the first user (e.g., a doctor) may provide input to create a medical conversation application mentioned above. The first user may provide various other inputs as well, such as an input specifying the first user's area of practice (e.g., hand surgeon, veterinarian, patent attorney, etc.), input specifying one or more digital conversational characters to be created for the given type of visual conversation application, among other examples.

At block 404, back-end platform 102 may then receive data from the first user's computing device 112 in order to create a given type of visual conversation application. Back-end platform 102 may receive this data at various times. For instance, while accessing a view of the content authoring tool, the first user may input one or more selections to create a medical conversation application and specify the first user's area of practice. Back-end platform 102 may then receive data from the first user's computing device 112 after the first user inputs the one or more selections or each time the first user inputs a given selection. Back-end platform 102 may receive this data at various other times as well (e.g., each time the first user inputs a selection).

At block 406, back-end platform 102 may generate a set of conversational content that may be used to define conversational content for a digital conversational character. Each conversational content in the set of conversational content may generally comprise (1) a pre-populated question that a given digital conversational character is capable of responding to during an interactive conversational session, and (2) a corresponding pre-populated response for the given digital conversational character to the pre-populated question. Depending on the type of visual conversation application being created (and perhaps the type of digital conversational character being created and employed for an interactive conversational session), the set of conversational content that is generated may take various forms.

As one possibility, the set of conversational content that is generated may comprise casual "chit-chat" conversational content that generally includes (1) a pre-populated casual question that may come up during any interactive conversational session between a given digital conversational character and a second user (e.g., a patient, a client, etc.) and (2) a pre-populated corresponding response to the casual question. For example, casual chit-chat conversational content may include a pre-populated question about the weather (e.g., "What's the weather?", "What will the weather be like tomorrow?", etc.) and a corresponding pre-populated response to the question. As another example, casual chit-chat conversational content may include a pre-populated greeting question (e.g., "Hi, how are you?", "What's up?", etc.) and a corresponding pre-populated response to the question.

In some implementations, casual chit-chat conversational content may include multiple pre-populated responses that each correspond to a given pre-populated casual question. In this respect, if a digital conversational character is asked the same question (e.g., "How are you?") multiple times during an interactive conversational session with a second user, the digital conversational character may be configured to respond differently each time with any one of the pre-populated responses.

Casual chit-chat conversational content may include other pre-populated questions and responses as well.

As another possibility, the set of conversational content that is generated may comprise "general" conversational content that includes a pre-populated question specific to a given profession (but not necessarily to a given area of practice of a given profession) and a corresponding pre-populated response to the question. For example, in the context of the medical profession, general conversational content may include a pre-populated medical question about a specific drug commonly prescribed by various types of doctors (e.g., "What are the side effects of amoxicillin?") and a corresponding pre-populated response to the question. As another example, in the context of the legal profession, general conversational content may include a pre-populated question about a legal term (e.g., "What is a summary judgment?") and a corresponding pre-populated response to the question. General conversational content may include other pre-populated questions and responses as well.

As yet another possibility, the set of conversational content that is generated may comprise specific "business" conversational content that includes a pre-populated question specific to a given area of practice of a given profession and a corresponding pre-populated response to the question. For example, specific conversational content may include a specific pre-populated question about hand surgery (e.g., "What does a hand surgery procedure involve?") and a corresponding pre-populated response to the question. As another example, specific conversational content may include a specific pre-populated question about patent law (e.g., "How much does it cost to file a patent application?") and a corresponding pre-populated response to the question. Specific conversational content may include other pre-populated questions and responses as well.

At still another possibility, the set of conversational content that is generated may comprise personal "rapport" conversational content that includes a pre-populated personal rapport question about a given professional and a corresponding pre-populated response to the question. For example, personal rapport conversational content may include a corresponding pre-populated personal question about a given doctor (e.g., "Do you have any kids?", "How old are you?", etc.) and a corresponding pre-populated response to the question. Personal rapport conversational content may include other pre-populated questions and responses as well.

One of ordinary skill in the art will appreciate that the set of conversational content that is generated may take various other forms as well.

Further, a corresponding pre-populated response for the given digital conversational character to a pre-populated question included in the given conversational content may take various forms. For instance, a corresponding pre-populated response to a pre-populated question may take the form of a text response (e.g., a string comprising one or more alphanumeric characters), an audio response, a video response, an image response (e.g., a visual aid), an interactive response (e.g., quiz, survey, etc.), or a combination thereof, among other possibilities. As one specific example, a response to the question "How do I know if I have the flu?" may take the form of a text and/or an audio response (e.g., "Do you have a fever?"), a video response (e.g., a video illustrating common flu-like symptoms), and/or an interactive response (e.g., an interactive survey to see if a patient has flu-like symptoms).

In some instances, a corresponding pre-populated response to a pre-populated question may be associated with an expression and/or movement to add context (e.g., sentiment, behavior, etc.) to the response. For example, a response to the question "How do I know if I have the flu?" may comprise an audio response (e.g., "Do you have a fever?") and the audio response may be associated with a facial expression (e.g., a concerned look) and body language (e.g., leaning forward movement). Other examples are possible as well.

One of ordinary skill in the art will appreciate that a corresponding pre-populated response to a question included in the given conversational content may take various other forms as well. One of ordinary skill in the art will also appreciate that the pre-populated questions and/or responses may be modified by the first user to tailor the questions and/or response to a given type of visual conversation application.

In practice, back-end platform 102 may tag each pre-populated response and/or question with one or more labels to associate the pre-populated response and/or question with a given type of conversational content, such that each pre-populated response and/or question can be referenced from a given datastore. Further, in practice, the set of conversational content that is generated may be intentionally limited to a given number of questions and responses and targeted such that the set of conversational content provides a set of relevant and targeted questions and responses that are applicable to the given type of visual conversation application that the first user wishes to create. For instance, for a medical professional (e.g., a doctor) who wishes to create a medical conversation application, back-end platform 102 may generate a set of conversational content that provides a set of relevant and targeted questions and responses that are generally applicable to conversations between a medical professional and a patient, or perhaps more specifically to conversations between a given type of medical profession (e.g., a hand surgeon) and a patient.

Further yet, in practice, while the set of conversational content that is generated may be intentionally limited to a given number of questions and responses, back-end platform 102 may reference data from various sources, such as the Internet, or one or more datastores in order to enable the first user to define questions and responses using one or more variable states. For example, back-end platform 102 may reference data from the Internet or perhaps a datastore that stores information about the hours of operation of various businesses, which may enable a first user to define a response using an "hours" variable to create the response "The surgical center is open from 9 am to 5 pm." As another example, back-end platform 102 may reference data from the Internet or perhaps a datastore that stores information about the weather in various locations, which may enable a first user to define a response using a "weather" variable, a "date" variable, and/or "location" variable to create the response "The weather tomorrow in Los Angeles will be 70 degrees and sunny." Back-end platform 102 may reference various other data or reference data from various other sources as well.

It should be understood that, in some implementations, the set of conversational content that is generated may not be intentionally limited to a given number of questions and responses such that the first user may have more options to define questions and responses for a given digital conversational character that may be created for a given type of visual conversation application.

After a set of conversational content is generated, the set of conversational content may be used to define the digital conversational character for the given type of visual conversational application being created. The first user may facilitate defining the digital conversational character for the given type of visual conversational application in various manners.

As one possibility, the first user may create a given digital conversational character for the given type of visual conversational application. The first user may create a given digital conversational character in various ways. As one example, the first user may select, via the first user's computing device 112 running the content authoring tool, a digital conversational character from a group of pre-defined and/or previously created digital conversational characters (such as, for example, the digital conversational characters shown in FIGS. 3, 7, 8, and 9). For instance, referring back to FIG. 5, the first user may use the left or right arrows in preview region 570 to select a digital conversational character from a group of pre-defined and/or previously created digital conversational characters. In some instances, the selected digital conversational character's appearance may be further customizable to make the character more or less realistic, animated, serious, happy, etc.

As another example, the first user may create a new digital conversational character using various editing tools, importing an existing image, or capturing an image (possibly a 3D image) of an individual using a camera (e.g., a camera coupled to the first user's computing device, or a camera of a 3D imaging system, etc.). In this respect, the first user may create a new digital conversational character for a visual conversational application that may be digital representation of a real human (e.g., the first user).

One of ordinary skill in the art will appreciate that the first user may create a new digital conversational character in various other ways and may be defined at various times. Further, in line with the discussion above, one of ordinary skill in the art will appreciate that the first user may create a single digital conversational character for a given type of visual conversation application or multiple digital conversational characters for a given type of visual conversation application, in which case, each given digital conversational character may be defined to ask and/or respond to certain questions or types of questions.

The first user may facilitate defining the digital conversational character for the given type of visual conversational application in various other manners as well. For example, as another possibility, the first user may facilitate defining conversational content for a created digital conversational character. For instance, as described in more detail below, the first user may input a response for the created digital conversational character and one or more questions corresponding to the response. The first user may facilitate defining conversational content for a created digital conversational character in various ways.

In one implementation, the first user may facilitate defining conversational content for a created digital conversational character by selecting conversational content theme from the set of conversational content themes that were generated by back-end platform 102. For instance, the first user may input a selection to include casual "chit chat" conversational content theme for a digital conversational character and back-end platform 102 may receive the first user's input. In line with the discussion above, in some instances, the selected conversational content may be further customizable such that a given question and/or response to the given question included in the selected conversation content theme may be modified by the first user.

In another implementation, the first user may facilitate defining conversational content for a created digital conversational character by using the content authoring tool to add new conversational content for the created digital conversational character. The first user may add new conversational content for the created digital conversational character in various manners.

As one example to illustrate, referring back to FIG. 5, view 500 depicts a view of the content authoring tool to add new conversational content for a digital conversational character. As shown, view 500 includes various elements, such as menu 510, theme data field 520, sentiment data field 530, response data field 540, question data fields 550 and 560, and preview region 570. The first user may interact with one or more of these elements in order to add new conversational content for a digital conversational character that has been created, where the new conversational content may comprise an appropriate response for the digital conversational character that corresponds to similar types of questions that may be asked in an interactive conversational session between a second user (e.g., a patient, a client, etc.) and the digital conversational character.

In general, menu 510 may enable the first user to navigate to a different view of the content authoring tool (or perhaps an entirely different tool, such as an administrative tool). Menu 510 may take various forms. For example, as shown in FIG. 5, menu 510 may comprise a pull-down menu that may be used to request access to another view (or a different tool). As another example, menu 510 may include a menu bar that is displayed horizontally across the top of view 500.

As yet another example, menu 510 may include one or more individual icons, such as an account icon that may be selected to view the first user's account settings and/or credentials. Menu 510 may take various other forms as well.

Theme data field 520 may also take various forms. For instance, as shown in FIG. 5, Theme data field 520 may comprise a pull-down menu that enables the first user to select a type of conversational content being added for a digital conversational character. In one example, the type of conversational content being added for a digital conversational character may be casual "chit-chat" conversational content theme described above (e.g., How's the weather?). In another example, the type of conversational content being added may be "general" conversational content theme, specific "business" conversational content theme or personal "rapport" conversational content theme described above. Theme data field 520 may take various other forms as well. For instance, theme data field 520 may comprise a text box that enables the first user to input the type of conversational content being added for a digital conversational character.

Sentiment data field 530 may also take various forms. For instance, as shown in FIG. 5, sentiment data field 530 may comprise a pull-down menu that enables the first user to select a type of sentiment that can be associated with a response in order to add context to the response. An example type of sentiment may include a negative sentiment (e.g., sad, angry, concerned, etc.), a neutral sentiment, or a positive sentiment (e.g., happy, excited, etc.), among other possibilities. In one particular example, the first user may select a negative sentiment (e.g., sad) from sentiment data field 530 to associate the negative sentiment with the response "I'm sorry you have been sick all morning." Sentiment data field 530 may take various other forms as well. For instance, sentiment data field 530 may comprise a text box that enables the first user to input the type of sentiment that should be associated with a response.

Response data field 540 may take various forms as well. For instance, as shown in FIG. 5, response data field 540 may take the form of a text box that enables the first user to input an appropriate response for a digital conversational character to a question. For example, the first user may input "I'm good. Thanks for asking." in response data field 540 as an appropriate response to the question "how are you?"

In some implementations, in line with the discussion above, the first user may input a response in response data field 540 that may include one or more variable states. For example, as an appropriate response to the question "When is your office open?", the first user may input "The surgical center is open from $hours" in response data field 540. In this way, when a second user asks the question "When is your office open?" during an interactive conversational session with a digital conversational character created for a given type of visual conversational application, back-end platform 102 may determine the variable state "$hours" by referencing data from the Internet or a given datastore that stores information about the hours of operation of various businesses in order to fill in the hours of operation for the particular business in question, and then generate the appropriate response for the digital conversational character (e.g., "The surgical center is open from 9 am to 5 pm on Thursday.", "The surgical center is open from 9 am to 1 pm on Saturday.", etc.).

As another example, as an appropriate response to the question "What's the weather?", the first user may input "The weather $date in $location will be /url/weather ($date, $location)" in response data field 540. In this way, when a second user asks the question "What's the weather?" during an interactive conversational session with a digital conversational character created for a given type of visual conversational application, back-end platform 102 may generate the appropriate response for the digital conversational character by referencing data from a datastore (and/or perhaps a link to an Internet location) that provides information about the weather in order to fill in weather information, which may vary depending on the time of day and location of the second user (e.g., "The weather today in LA right now is 75 degrees and sunny.")

The first user may input a response in response data field 540 that may include various other variable states as well (e.g., "score" of a particular football game, "time" it takes to get to a particular location, etc.).

Further, in some implementations, the first user may input an amplitude of a response either in response data field 540 or in another data field (that may or may not be shown in FIG. 5). In general, an amplitude of a response may add additional context to a response that may be input in response data field 540 by defining an expression for a digital conversational character that is associated with the response (or a particular word or phases within the response). The amplitude of a response may take various forms. For instance, an amplitude of a response may be numerical value from a scale of 1 to 5, where a numerical value of 1 may correspond to an extremely mellow expression and a numerical value of 5 may correspond to an extremely animated expression. The amplitude of a response may take various other forms as well and depending on the form, the response data field 540 may take various other forms as well.

Still further, in some implementations, the first user may "mark-up" input of a response in response data field 540 to assign an emotion, expression, and/or body language to a particular word or phrase in the response for a digital conversational character. For instance, the first user may mark-up input of a response in response data field 540 by highlighting (and/or underlining) portions of the inputted response and selecting a cue to assign a particular emotion, expression, and/or body language to the highlighted portions of the inputted response. The first user may "mark-up" input of a response in response data field 540 in various other manners as well, and depending on the manner, response data field 540 may take various other forms.

In practice, back-end platform 102 may translate a marked-up input from response data field 540 into one or more markup languages that may be part of a script that can be provided to the second user's computing device 114, examples of which may include Time Text Markup Language ("TTML"), Speech Synthesis Markup Language, ("SSML") and/or a Kinesics Animation Markup Language ("KAML") that can annotate an emotion, an expression, and/or body language assigned to a particular word or phrase in response data field 540. One of ordinary skill in the art will appreciate that, back-end platform 102 may translate a marked-up input from response data field 540 in various other manners as well.

In some instances, the first user may "act in" an appropriate emotion, expression, and/or body language for a digital conversational character in order to create a credible response to a question. For instance, the first user may capture various emotions, expressions, and/or body language for a response using a camera and/or microphone which may or may not be coupled to the first user's computing device 112. Back-end platform 102 may receive the captured data, and then based on the captured data, cause the first user's computing device to present a view that includes a sentiment for the response that may be populated in sentiment data field 530, an amplitude for the response and/or a mark-up of the response (or a particular word or phrase within the response) that may be populated in response data field 540 (or one or more other data fields). The first user may act in an appropriate emotion, expression, and/or body language for a response in various other manners as well, and depending on the manner, response data field 540 may take various other forms.

It should be understood that the first user may input a response in response data field 540 in various other manners and response data field 540 may take various other forms as well.

Further, in some implementations, there may be more than one response data field that may enable the first user to input a primary response and one or more secondary responses to a particular question that may be asked by a second user in an interactive conversational session. In some instances, each respective response may be associated with a given interaction mode that may specify a level of detail in which a digital conversational character may respond and interact with a second user during an interactive conversational session. For instance, the disclosed content authoring tool may provide a primary response data field that is associated with a non-personal mode and a secondary response data field that is associated with a personal mode. Generally speaking, the primary response data field that is associated with a non-personal mode may correspond to a general response to a question that is not specific to a particular user (e.g., client, patient, etc.), whereas the secondary response data field that is associated with a personal mode may correspond to a particular response to a question that is specific to a particular user (e.g., client, patient, etc.).

In one particular example, view 500 may include two response data fields that may enable the first user to input a non-personal response in a first response data field (e.g., response data field 540) and a personal response in a second response data field (not shown). Specifically, for the question "What time is my surgery next week?", the first user may input a non-personal response in a first response data field (e.g., "Please check your email.") and personal response in a second response data field (e.g., "Your surgery is scheduled for */appt with Dr. G.", where variable state */appt may be dynamically determined to be "9 am Wednesday morning" based on the identity of the second user and referencing a scheduling calendar for that the second user). An interaction mode (e.g., "personal," "non-personal," etc.) for an interactive conversational session between a second user and a digital conversational character may be determined in various manners described in more detail below, which may determine the appropriate response (e.g., personal response vs. non-personal response) to a question asked by a second user during an interactive conversational session.

Response data fields described herein may take various other forms as well.

Question data fields 550 and 560 may also take various forms. For instance, as shown in FIG. 5, question data fields 550 and 560 may each take the form of a text box that enables the first user to input respective questions that correspond to a response that may be input in response data field 540. In this respect, respective questions that are input in question data fields 550 and 560 may be variations of similar types of questions that may provoke the same response input in response data field 540. For example, for the response "I'm good. Thanks for asking" that may be input in response data field 540, the first user may input the question "How are you?" in question data field 550 and "How are you doing?" in question data field 560.

In some implementations, the first user may identify the question as a condition (vs. a question) and input respective conditions in question data fields 550 and 560 that each correspond to a response input in response data field 540. A respective condition that the first user may input in a question data field may take various forms. For example, the first user may input a "speech unintelligible" condition in question data field 550 that corresponds to a response input in response data field 540 (e.g., "Could you please repeat your question? I can't understand you."). In this respect, if the second user interacting with a digital conversational character created for the given type of visual conversation application asks a question during an interactive conversational session that cannot be understood, the digital conversational character may respond with the response that was input in response data field 540 (e.g., "Could you please repeat your question? I can't understand you.").

As another example, the first user may input a "speech inappropriate" condition in question data field 550 that corresponds to a response input in response data field 540 (e.g., "Please ask me a more appropriate question.") In this respect, if the second user interacting with a digital conversational character created for the given type of visual conversation application asks a question during an interactive conversational session that may be inappropriate, the digital conversational character may respond with the response that was input in response data field 540 (e.g., "Please ask me a more appropriate question.").

As yet another example, the first user may input a "fallback" condition in question data field 550 that corresponds to a response input in response data field 540 (e.g., "I'm sorry, I'm not sure, ask me something else.") In this respect, if the second user interacting with a digital conversational character created for the given type of visual conversation application asks a question during an interactive conversational session that the first user has not authored conversational content for the digital conversational character to answer, the digital conversational character may respond with the response that was input in response data field 540 (e.g., "I'm sorry, I'm not sure, ask me something else.").

In some implementations, the first user may input a "fallback" condition in question data field 550 without any input in response data field 540. In this respect, if the second user interacting with a digital conversational character created for the given type of visual conversation application asks a question during an interactive conversational session that the first user has not authored conversational content for the digital conversational character to answer, the digital conversational character may respond with a response from a set of appropriate responses (e.g., "I'm sorry, I'm not sure, ask me something else.", "I don't know, ask me a different question.", etc.).

Further, in some instances, during or after an interactive conversational session between the second user and a digital conversational character, back-end platform 102 may send a notification to the first user's computing device 112 (e.g., email, text, direct message, etc.) to notify the first user that the second user has asked a particular question during an interactive conversational session that the first user has not authored conversational content for the digital conversational character to answer. In practice, this notification may be presented to the first user when the first user later accesses the disclosed content authoring tool on the computing device 112. In one embodiment, this notification may comprise the unanswered question in a question field with an empty response field and a prompt for the first user to fill in the response field. The first user may then update conversational content for the given type of visual conversation application that was created, such that the next time the particular question (or a similar type of question) is asked during an interactive conversational session, the digital conversational character can provide a response corresponding to the updated conversation content for the given type of visual conversation application.

A respective condition that the first user may input in a question data field may take various other forms as well. Further, it should be understood that the first user may input respective questions and/or conditions in question data fields 550 and 560 in various manners similar to the manners described above with respect to response data field 540.

In practice, back-end platform 102 may validate the respective questions and/or conditions that are input in question data fields 550 and 560 to ensure the respective questions and/or conditions do not overlap with other questions and/or conditions that have already been defined for the digital conversational character created for the given type of visual conversation application. Back-end platform 102 may validate the respective questions and/or conditions at various times (e.g., each time a given question or condition has been input in a given question data field, after all the respective questions or conditions have been input in the question data fields, etc.).

One of ordinary skill in the art will appreciate that, in some implementations, the first user may add an additional question data field (e.g., by selecting the "Add Training Phrase" control button shown in FIG. 5) to input an additional question or condition that corresponds to the response input in response data field 540. Similarly, one of ordinary skill in the art will appreciate that in other implementations, there may be only one question data field (e.g., question data field 550 but not question data field 560) for the first user to input a question or condition that corresponds to the response input in response data field 540.

In accordance with the present disclosure, preview region 570 may take various forms as well. For instance, as shown in FIG. 5, preview region 570 may include a preview window and controls (e.g., play and pause controls) that enable the first user to input an option to preview a response for a digital conversational character in the preview window at any point while the first user facilitates defining conversational content for the digital conversational character (e.g., while inputting a response in response data field 540). In some implementations, the first user may be able to preview a response and the sentiment, expression, and/or body language associated with the response. This may allow the first user to fine-tune the response along with the associated sentiment that may be input in sentiment data field 530 and/or the associated expressions (indicated by the amplitude of the response and/or mark-up of the response that may be input in response data field 540), such that the response for the digital conversational character can be properly conveyed to a second user during an interactive conversational session.

After the first user inputs data in one or more elements that are presented in view 500 (e.g., theme data field 520, sentiment data field 530, response data field 540, and/or question data fields 550 and 560, etc.), the first user may send a request, via the first user's computing device 112, to add new conversational content comprising the inputted data for a digital conversational character that has been created for the given type of visual conversation application (e.g., by selecting the "Submit" control button shown in FIG. 5). In some embodiments, the new conversational content is made available in real time (e.g., substantially immediately) so that a second user can utilize the new input. Further, after the first user facilitates defining conversational content for a digital conversational character that has been created for the given type of visual conversation application, the first user may optionally create one or more additional digital conversational characters for the given type of visual conversation application and facilitate defining conversational content for each digital conversational character using the elements described above.

At block 408, back-end platform 102 may receive, from the first user's computing device, data that defines the digital conversational character for the given type of visual conversation application being created. For instance, back-end platform 102 may receive, from the first user's computing device 112, data that defines the conversational content for a digital conversational character that has been created for the given type of visual conversation application. Back-end platform 102 may receive such data at various times (e.g., each time the first user defines a question and/or response for a digital conversational character, after the first user defines all conversational content for a digital conversational character, etc.). In some implementations, after the first user defines conversational content for the digital conversational character(s) created for the given type of visual conversation application, the first user may input an indication to publish the given type of visual conversation application. Back-end platform 102 may then receive data corresponding to such indication.

In turn, at block 410, based on the received data that defines the given type of visual conversation application, back-end platform 102 may create the given type of visual conversation application, which may allow the second user (e.g., a patient, a client, etc.) to access the given type of visual conversation application via the second user's computing device (e.g., computing device 114) to interact with a digital conversational character that was created to interact with the second user in an interactive conversational session. Back-end platform 102 may create the given type of visual conversation application in various manners.

In practice, after the first user inputs the respective questions and/or conditions using the authoring tool on the computing device 112, back-end platform 102 may receive data corresponding to the questions and/or conditions that are input in question data fields 550 and 560, and then analyze the scope of the questions and/or conditions to identify multiple ways in which the second user may ask similar questions (or trigger the conditions) that may provoke the response that was input in response data field 540. For example, back-end platform 102 may receive data corresponding to the questions "How are you?" and "How are you doing?" that were input in question data fields 550 and 560, respectively, and then analyze the scope of these questions. In this respect, the second user interacting with a digital conversational character created for a given type of visual conversation application may ask similar questions (e.g., How are you feeling?) during an interactive conversational session that may provoke the same response from the digital conversational character.

In one implementation, in order to perform this analysis, creating the given type of visual conversation application may involve back-end platform 102 defining one or more predictive models to predict an appropriate response for the digital conversational character that corresponds to a question asked by the second user in an interactive conversational session (e.g., How are you feeling?). A given predictive model that may be defined to predict an appropriate response for the digital conversational character may take various forms.

As one possibility, a given predictive model may take the form of a supervised classification model. The supervised classification model may take various forms, examples of which may include a Naive Bayes model, a random forest model, a decision tree model, gradient-boosted tree model (such as those implemented using the XGBoost library), and a logistic regression model, as some non-limiting examples. A given predictive model may take various other forms as well (including but not limited to an unsupervised model).

Further, a given predictive model may be defined in various manners. As one example, a given predictive model may be defined with various kinds of "training data," examples of which may include conversational content that comprises a response that was input in response data field 540 and the corresponding questions that were input in questions data fields 550 and 560 and/or information about the first user (e.g., the first user's profession and/or area of practice, etc.). Based on the training data, the given prediction model may be defined by parsing words or phrases from the conversational content (e.g., a response that was input in response data field 540 and the corresponding questions that were input in questions data fields 550 and 560) and classifying each word or phrase in a given conversational category (e.g., age, profession, dosage, frequency, person, location, organization, date, etc.). In some implementations, depending on the type of predictive model being defined, back-end platform 102 may assign weights to each parsed word or phrase, which may improve the predictive model in predicting an appropriate response for the digital conversational character that corresponds to a question asked by the second user in an interactive conversational session. For instance, words or phrases used in a given profession (e.g., surgery, injection, etc.) may be assigned a greater weight than connective words. Back-end platform 102 may define a given predictive model in various other manners as well.

In turn, back-end platform 102 may deploy the given predictive model to predict an appropriate response for the digital conversational character that corresponds to a question asked by the second user in an interactive conversational session. For instance, the given predictive model may be configured to (1) receive a given question asked by the second user during an interactive conversational session as the model's input (perhaps along with other data, such as information about the first and/or second user, information about the digital conversational character, etc.), and then (2) evaluate the input data to output a prediction of whether a given response is appropriate for the digital conversational character based on the given question asked by the second user. This output may take various forms.

As one possibility, the given predictive model may be configured such that each time it evaluates input data to render a prediction of whether a given response is appropriate for the digital conversational character, the given predictive model may output a binary indication of whether or not a given response is appropriate for the digital conversational character. As another possibility, the given predictive model may be configured such that each time it evaluates input data to render a prediction of whether a given response is appropriate for the digital conversational character, the given predictive model may output a metric that reflects the predicted relevance of the given response (e.g., a value from 0 to 100), which may then be compared to a threshold to make a binary determination of whether given response is appropriate for the digital conversational character based on the given question asked by the second user. The output of the given predictive model may take various other forms as well.

Back-end platform 102 may create the given type of visual conversation application in various manners.

In accordance with the present disclosure, in some implementations, based on the received data that defines the digital conversational character for the given type of conversation application, back-end platform 102 may update the set of conversational content that may be generated to define conversational content for a given digital conversational character. For instance, based on the received data, back-end platform 102 may add, modify, and/or delete conversational content (e.g., a question and/or a response) from a set of conversational content that may be generated to define conversational content for a given digital conversational character).

Further, in some implementations, back-end platform 102 may store the received data that defines the digital conversational character for the given type of conversation application and/or the updated set of conversational content that may be used to define conversational content for a given digital conversational character in one or more datastores (e.g., a datastore stored in data storage 204, or a datastore from an external data source). One of ordinary skill in the art will appreciate that back-end platform 102 may store such data in various manners.

Once back-end platform 102 creates the given type of visual conversation application (e.g., medical conversation application, interview conversation application, product conversation application, etc.), the disclosed process may transition from the authoring phase to the rendering phase, which generally involves a second user (e.g., a patient, a client, etc.) accessing the given type of visual conversation application to interact with a digital conversational character in an interactive conversational session. The rendering phase of the disclosed process may take various forms and the functions carried out in the second phase may be carried out in various manners.

B. Example Rendering Phase

Figure 6:
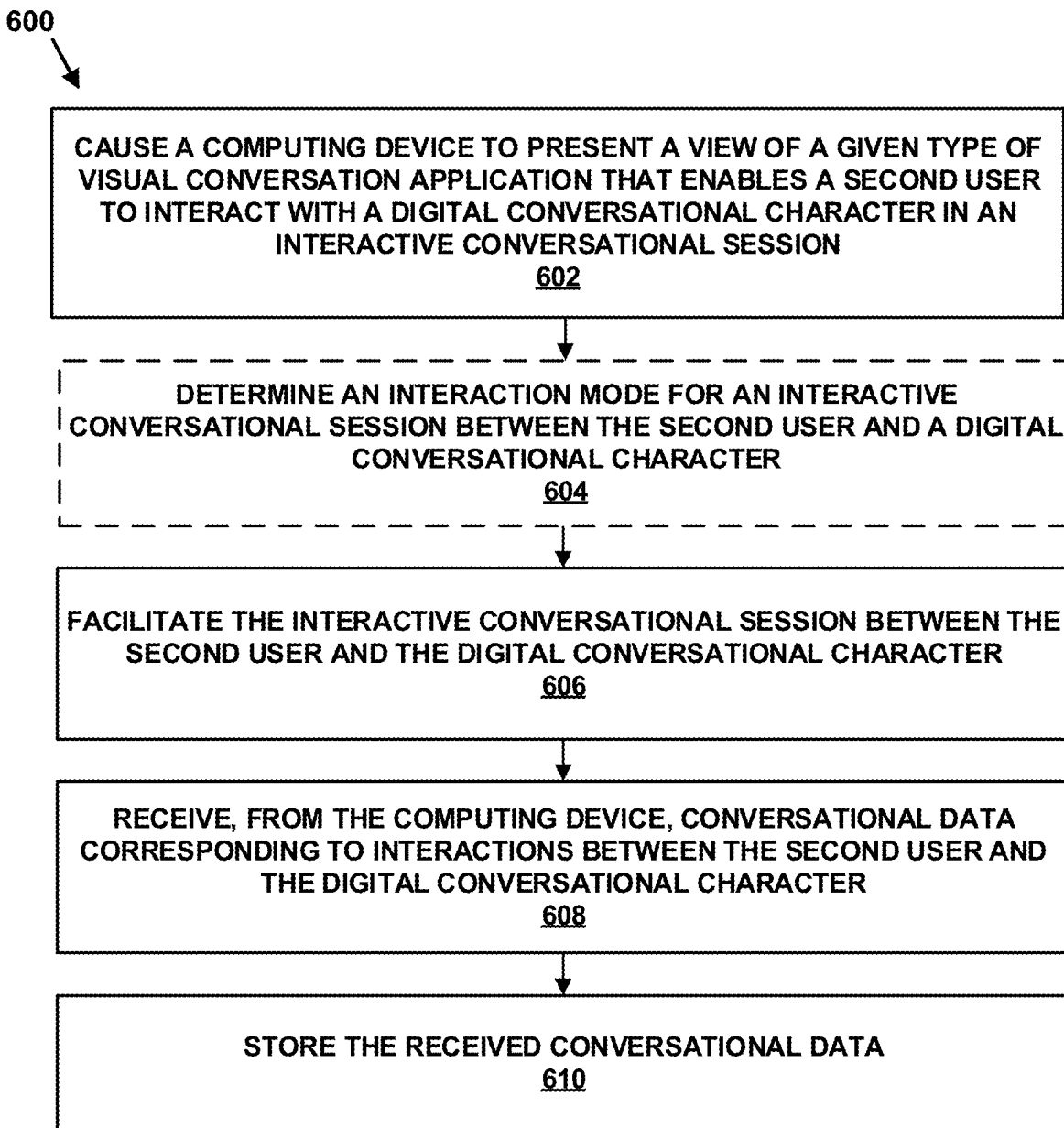
FIG. 6 depicts an example flow chart for the rendering phase of the present disclosure.

Method 600 shown in FIG. 6 presents an embodiment of a method of a rendering phase that can be implemented within an operating environment including or involving, for example, the operating system 100 of FIG. 1, the computing platform 200 of FIG. 2A, and/or the computing device 201 of FIG. 2B. Method 600 may include one or more operations, functions. Or actions as illustrated by one or more blocks 602-610. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

According to an example implementation, the rendering phase of the disclosed process may begin with the second user (e.g., a patient, a client, etc.) accessing, via the second user's computing device (e.g., computing device 114), a given type of visual conversation application that has been created by the first user (e.g., medical conversation application, interview conversation application, product conversation application, etc.). The second user may request access to the given type of visual conversation application in various manners.

As one possibility, the second user may request access to the given type of visual conversation application by launching a native application on the second user's computing device 114 and logging into the second user's account or directing a web browser on the second user's computing device 114 associated to a uniform resource locator (URL) for the given type of visual conversation application and logging into the second user's account, either of which may cause the second user's computing device 114 to send a request to back-end platform 102 to access the given type of visual conversation application.

In some implementations, the second user may use a unique code provided by the first user to create and log into the second user's account to access the given type of visual conversation application. The unique code may take various forms. For instance, the unique code may comprise alphanumerical characters and may be associated with the second user and/or may be associated with a specific conversational session between the second user and a digital conversational application created for the given type of visual conversational application being accessed. The unique code may take various other forms as well.

As another possibility, the second user may request access to the given type of visual conversation application by launching a third-party application associated with the given type of visual conversation application. For instance, the second user may access the contacts list from a contacts application that may include contact information for a given professional and/or a digital conversational character associated with a given professional and then input a selection to contact the given professional or digital conversational character (e.g., via text message, phone call, FaceTime', etc.).

As yet another possibility, the second user may request access to the given type of visual conversation application based on the location of the second user. For instance, the second user may receive a notification that a given professional or a digital conversational character associated with a given professional is available to interact with the second user when the second user is within a certain location (for example, via geofencing notification). The second user may then provide an input requesting access to the given type of visual conversation application to interact with the digital conversational character.

As a further possibility, the second user may request access to the given type of visual conversation application by scanning or taking a picture of a given professional's business card (which in some implementations may comprise a QR code) via the second user's camera (e.g., camera 262 of computing device 201). Back-end platform 102 may then launch a native application on the second user's computing device 114, launch a web browser on the second user's computing device 114 associated to a uniform resource locator (URL) for the given type of visual conversation application, or perhaps launch a third-party application to install the given type of visual conversation application on the second user's computing device 114 or add the given professional (or a digital conversational character associated with the given professional) to the second user's contact list.

The second user may request access to the given type of visual conversation application in various other manners as well.

At block 602, after receiving a request from the second user's computing device 114 to access the given type of visual conversation application, back-end platform 102 may cause the second user's computing device 114 to present a view of the given type of visual conversation application that enables the second user to interact with a digital conversational character in an interactive conversational session. This view may take various forms.

Figure 7:
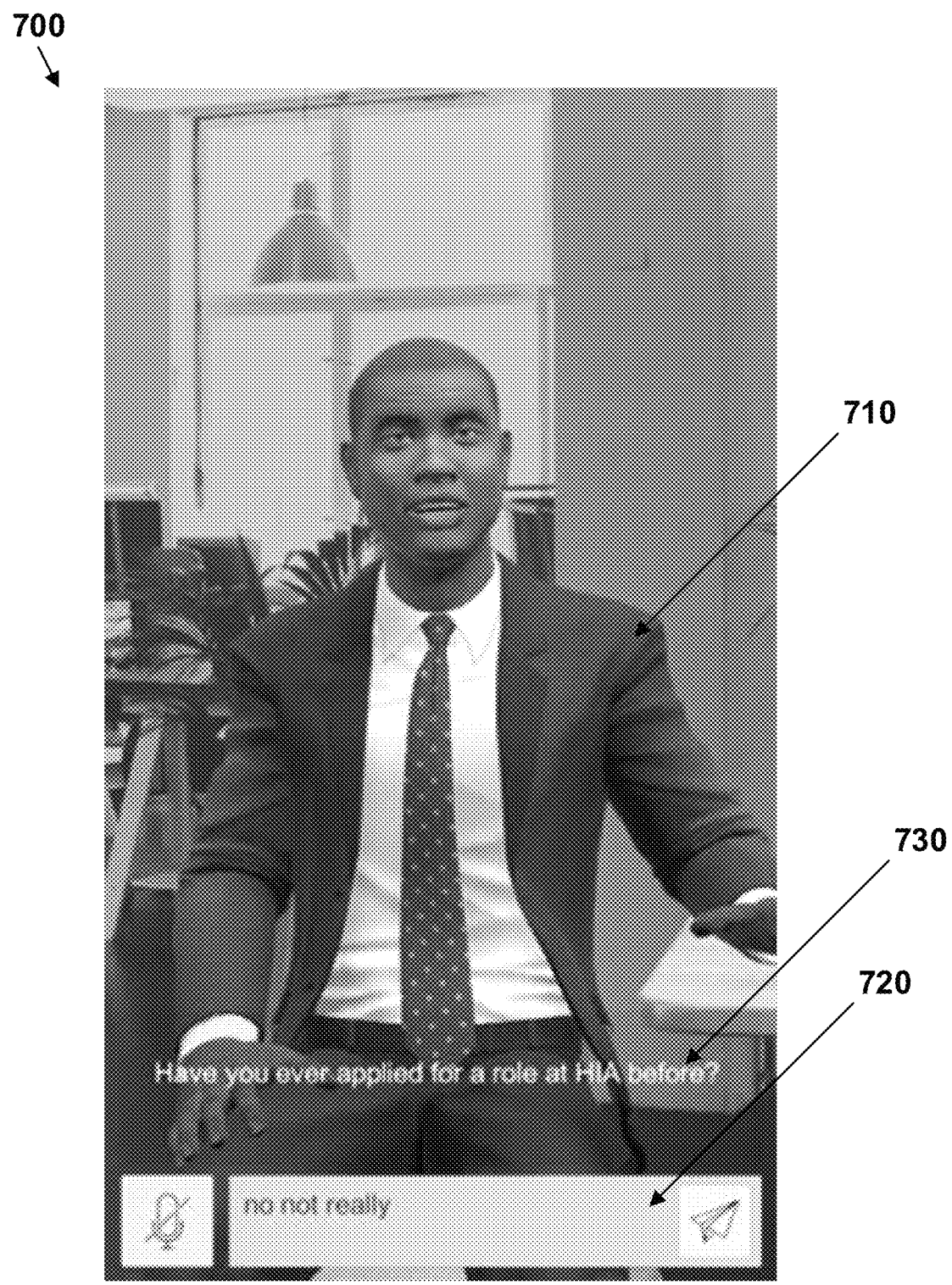
FIG. 7 depicts an example view of a given type of visual conversational application that may be presented to a computing device.

As one possibility, FIG. 7 depicts an example view 700 of a given type of visual conversation application (e.g., interview conversation application) that may be presented to enable the second user to interact with digital conversational character 710 during an interactive conversational session. As shown, view 700 may include various elements, such as input region 720 that may enable the second user to input a question or response (e.g., by inputting text) and textual display region 730 that may present a question or a response from digital conversational character 710. In particular, in response to a question from digital conversational character 710, which is displayed in textual display region 730 (e.g., "Have you ever applied for a role at HIA before?"), the second user may input a corresponding response in input region 720 (e.g., "no not really") by typing a response via the second user's computing device.

One of ordinary skill in the art will appreciate that view 700 may include additional elements not shown and/or more or less of the depicted elements. Further, one of ordinary skill in the art will appreciate that the view 700 may take various other forms as well.

Figure 8:
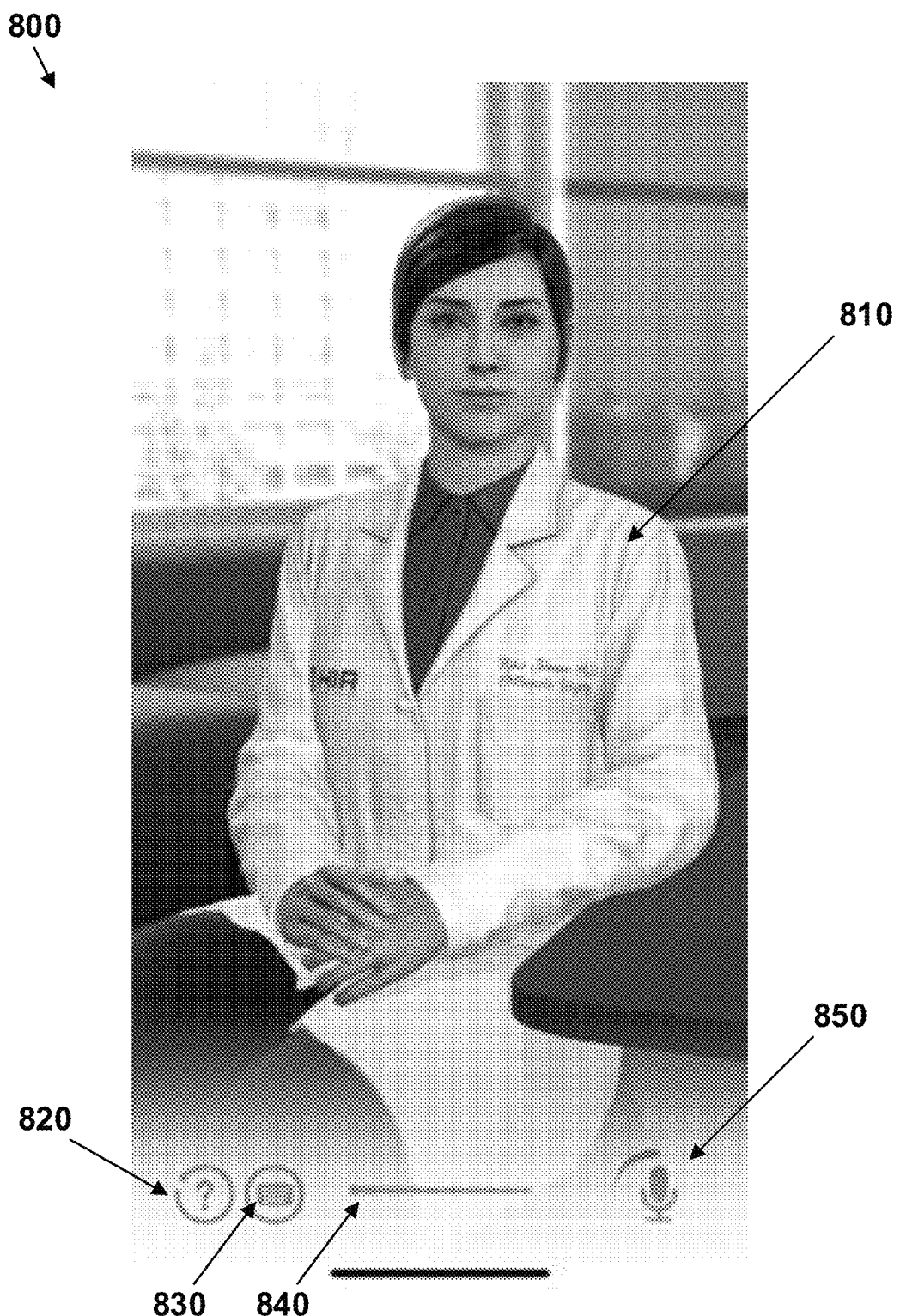
FIG. 8 depicts another example view of a given type of visual conversational application that may be presented to a computing device.

As another possibility, FIG. 8 depicts an example view 800 of a given type of visual conversation application (e.g., medical conversation application) that may be presented to enable the second user to interact with digital conversational character 810 during an interactive conversational session. As shown, view 800 may include various elements, such as repeat element 820, keyboard element 830, audio waveform display 840, and microphone element 850. These elements may take various forms.

In general, repeat element 820 may enable the second user to repeat a question or response from digital conversational character 810. For instance, in response to a selection of repeat element 820, back-end platform 102 (and/or the second user's computing device) may cause digital conversational character 810 to repeat a question or response that was previously uttered by digital conversational character 810. In some instances, in response to a selection of repeat element 820, back-end platform 102 and/or the second user's computing device) may cause digital conversational character 810 to rephrase a question or response in a different way to ensure that the second user understands the question or response uttered by digital conversational character 810. In other instances, the second user may input or utter a response (e.g., via keyboard element 830 or microphone element 850) requesting digital conversational character 810 to repeat or rephrase a question or response (e.g., "Can you say that again", "I didn't catch that", etc.) Repeat element 820 may take various other forms as well.

Keyboard element 830, which may enable the second user to input a question or response for digital conversational character 810, may take various forms as well. For instance, as shown, keyboard element 830 may take the form of a control button that, when selected, may cause the second user's computing device to provide an on-screen keyboard that allows the second user to input a question or response during an interactive conversational session with digital conversational character 810. Keyboard element 830 may take various other forms as well.

Similarly, microphone element 850, which may capture enable the second user to utter a question or response for digital conversational character 810, may take various forms as well. For instance, as shown, microphone element 850 may take the form of a control button that, when selected, may enable the second user to start recording a question or response for digital conversational character 810. Microphone element 850 may take various other forms as well.

Audio waveform display 840, which can provide a visual representation of audio (e.g., the second user's utterance) as it is being captured, may also take various forms. For instance, while the second user utters a question or response to digital conversational character 810, audio waveform display 840 may provide visual confirmation (e.g., an audio waveform visualizer) that the second user's voice is being captured. Audio waveform display 840 may take various other forms as well.

In practice, in some implementations, back-end platform 102 may be configured to receive the captured audio (e.g., the second user's utterance) and analyze the ambient background noise against the second user's utterance in order to isolate the background noise and parse the beginning of the second user's utterance as well as the end of the second user's utterance. Back-end platform 102 may in turn determine a response for the digital conversational character and cause the digital conversational character to respond to the second user's utterance.

One of ordinary skill in the art will appreciate that view 800 may include additional elements not shown and/or more or less of the depicted elements. For example, view 800 may include an inset display element (not shown) that enables the second user to see how the second user appears during an interactive conversational session, which may also allow the second user to verify that a video connection has been properly established for the interactive conversational session. As another example, view 800 may not include audio waveform display 840. Further, one of ordinary skill in the art will appreciate that the view 800 may take various other forms as well.

Figure 9:
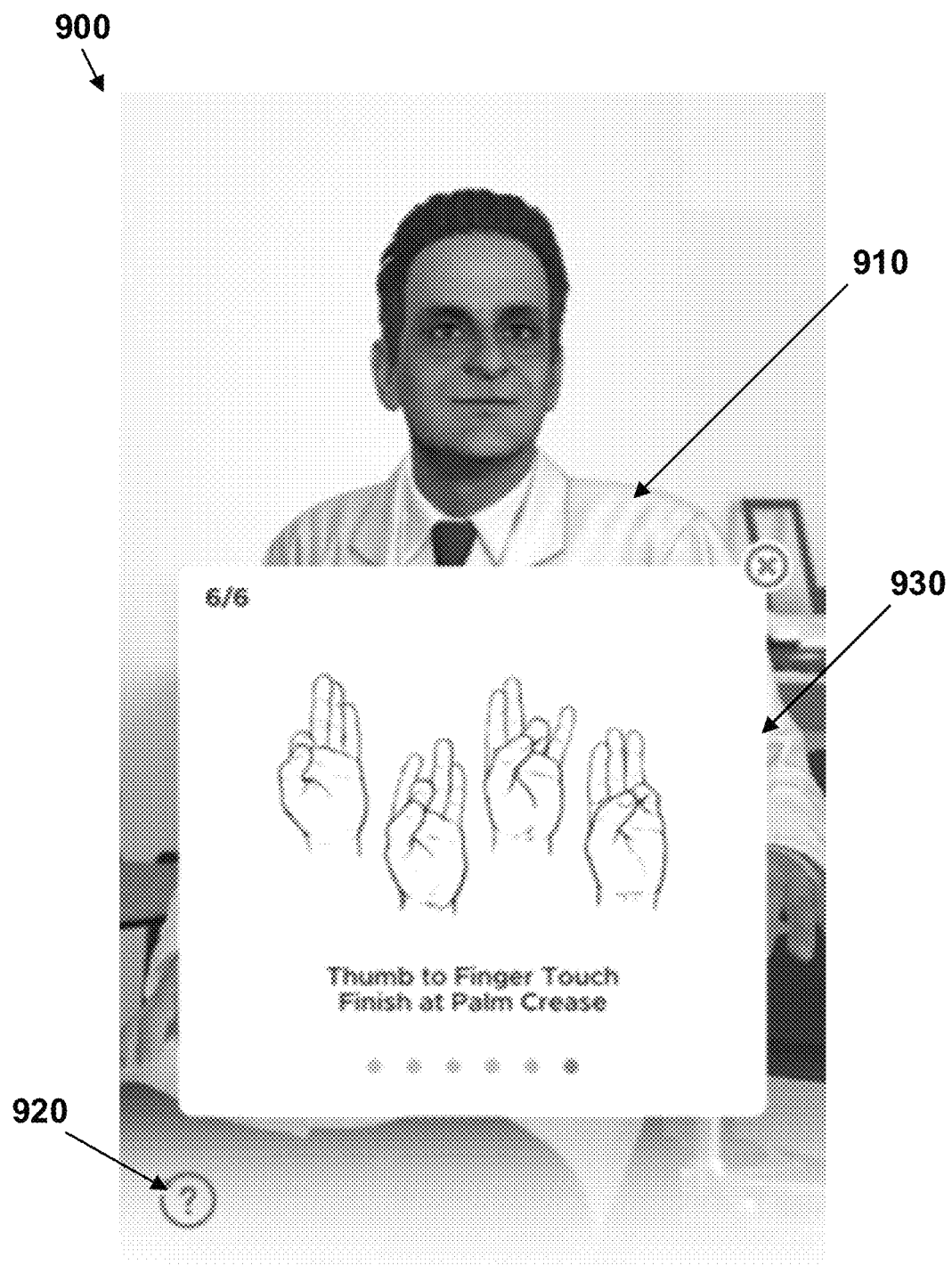
FIG. 9 depicts yet another example view of a given type of visual conversational application that may be presented to a computing device.

The view of the given type of visual conversation application that enables the second user to interact with a digital conversational character in an interactive conversational session may take various other forms as well. For example, as yet another possibility, FIG. 9 depicts an example view 900 of a given type of visual conversation application (e.g., medical conversation application) that may be presented to enable the second user to interact with a digital conversational character 910 during an interactive conversational session. As shown, view 900 may include various elements, such as repeat element 920 (which may take the form similar to repeat element 820 of FIG. 8) and instruction display element 930.

Instruction display element 930, which may generally display a response from digital conversational character 910 in the form of an instruction (e.g., a visual aid), may take various forms. For instance, as shown, in response to a second user's question regarding a medical procedure (e.g., "Will I need physical therapy after the operation?"), digital conversational character 910 may respond with an answer that may comprise interactive instructions regarding the medical procedure. The second user may interact with instruction display element 930 to read the instructions (e.g., by swiping instruction display element 930 left or right). Instruction display element 930 may take various other forms as well (e.g., an embedded video, image, audio recording, etc.)

The view of the given type of visual conversation application that enables the second user to interact with a digital conversational character in an interactive conversational session may take various other forms as well.

At block 604, after receiving a request from the second user's computing device to access a given type of visual conversation application, back-end platform 102 may optionally determine an interaction mode for an interactive conversational session between the second user and a digital conversational character. Back-end platform 102 may determine an interaction mode for an interactive conversational session between the second user and a digital conversational character in various manners.

As one possibility, back-end platform 102 may determine whether the second user is a registered user that has an account associated with the given type of visual conversation application or a guest user that does not have an account associated with the given type of visual conversational application. If the second user is a registered user, back-end platform 102 may determine that the interaction mode should be in personal mode for the interactive conversational session between the second user and a digital conversational character, in which case the digital conversational character may be configured to respond to the second user with a personal response as described above. On the other hand, if the second user is a guest user, back-end platform 102 may determine that the interaction mode should be in non-personal mode for the interactive conversational session between the second user and a digital conversational character, in which case the digital conversational character may be configured to respond to the second user with a non-personal response as described above.

As another possibility, back-end platform 102 may determine whether the second user is a paid subscriber or an unpaid subscriber for the given type of visual conversation application. If the second user is a paid subscriber, back-end platform 102 may determine that the interaction mode should be in personal mode for the interactive conversational session between the second user and a digital conversational character. On the other hand, if the second user is an unpaid subscriber, back-end platform 102 may determine that the interaction mode should be in non-personal mode.

As yet another possibility, for a given type of visual conversation application such as the medical conversation, back-end platform 102 may determine whether the second user has agreed to Health Insurance Portability and Accountability Act (HIPAA) terms and/or General Data Protection Regulation (GDPR) terms. If the second user has agreed to such terms, back-end platform 102 may determine that the interaction mode should be in personal mode for the interactive conversational session between the second user and a digital conversational character. On the other hand, if the second user has not agreed to such terms, back-end platform 102 may determine that the interaction mode should be in non-personal mode.

In practice, a given user's account (e.g., the second user's account) may be associated with various account information, examples of which may include account credentials (e.g., password), contact information (address, phone number), personal information (e.g., medical records, insurance information, social security number, information about family member, etc.), conversation history (e.g., past records of interactions with a digital conversational character), and/or payment-related information (e.g., subscription status, payment history, etc.), among other examples. In this respect, any account information associated with a given user (e.g., the second user) may be referenced by back-end platform 102 to make certain determinations disclosed herein.

Back-end platform 102 may determine an interaction mode for an interactive conversational session between the second user and a digital conversational character in various other manners as well.

At block 606, back-end platform 102 may then facilitate the interactive conversational session between the second user and the digital conversational character. For instance, back-end platform 102 may cause the digital conversational character to ask the second user a question or respond to the second user. Back-end platform 102 may also receive a second user's question or response during the interactive conversational session between the second user and the digital conversational character.

For example, with respect to FIG. 7, back-end platform 102 may cause digital conversational character 710 to ask the second user the question "Have you ever applied for a role at HIA before?", which may be presented in textual display region 730 (and perhaps uttered by digital conversational character 710). The second user may then input a response (e.g., "no not really") in input region 720 and/or utter a response that may be captured via a microphone of the second user's computing device. Back-end platform 102 may then receive the second user's response.

As another example, with respect to FIG. 9, back-end platform 102 may receive the second user's response "Will I need physical therapy after the operation?", which may be uttered by the second user. Back-end platform 102 may then cause digital conversational character 910 to utter the response "Generally, most patients perform home therapy. Here's a set of instructions on how to do home therapy" and also cause the second user's computing device to present a set of instructions associated with the response in instruction display element 930.

In some implementations, in line with the discussion above, depending on the determined interaction mode, the digital conversational character may be configured to provide a different response to a question asked by the second user during an interactive conversational session. For example, in personal mode, if the second user asks the question "What time is my surgery next week?" during an interactive conversational session, the digital conversational character may be configured to respond to the second user with the personal response, "Your surgery is scheduled for 9 am in the morning with Dr. G." In non-personal mode, the digital conversational character may be configured to respond to the same question with the non-personal response "Please check your email."

As another example, in personal mode, if the second user asks a question regarding an appointment, the digital conversational character may be configured to connect the second user to a scheduling system so that an appointment may be scheduled, re-scheduled, or cancelled. In some instances, the digital conversational character may be configured to schedule, re-schedule, or cancel an appointment for the second user. On the other hand, in non-personal mode, if the second user asks a question regarding an appointment, the digital conversational character may be configured to provide the second user contact information (e.g., a phone number) to schedule, re-schedule, or cancel an appointment. In case of an emergency, the digital conversational character may be configured to contact an emergency response team for the second user during an interactive conversational session, regardless of if it is in personal or non-personal mode.

In other implementations, in line with the discussion above, back-end platform 102 may facilitate an interactive conversational session between the second user and the digital conversational character based on the location of the second user. For example, if the second user's location is determined to be at or near a professional's office (e.g., a doctor's office), back-end platform 102 may facilitate an interactive conversational session between the second user and a digital conversational character, such that the second user can interact with the digital conversational character regarding a current visit with the professional (e.g., surgical procedure with the doctor) and obtain information from the digital conversational character regarding the current visit (e.g., patient information, patient medical history, privacy notices, insurance policies, etc.).

Further, in some implementations, back-end platform 102 may facilitate an interactive conversational session between the second user and the digital conversational character and, at some time during the interactive conversational session, back-end platform 102 may facilitate communications between the second user and a professional. For example, during an interactive conversational session between the second user (e.g., a patient) and the digital conversational character, back-end platform 102 may receive a response that indicates that the second user should consult a professional immediately (e.g., in the case of an emergency medical situation). Back-end platform 102 may in turn facilitate communications between the second user and a professional, such that the second user can communicate directly with the professional (e.g., via a phone call, text, email, etc.).

Further yet, in some implementations where multiple digital conversational characters are configured to interact with the second user, a given digital conversational character may be configured to respond with a transition phrase before the interactive conversational session transitions from the given digital conversational character to another digital conversational character.

Back-end platform 102 may facilitate an interactive conversational session between the second user and the digital conversational character in various other manners as well.

At block 608, back-end platform 102 may receive, from the second user's computing device, conversational data corresponding to interactions between the second user and the digital conversational character. For instance, back-end platform 102 may receive the second user's responses to the digital conversational character's questions and/or the second user's questions asked during an interactive conversational session with the digital conversational character.

Back-end platform 102 may receive such conversational data at various times. As one possibility, back-end platform 102 may receive the second user's responses and/or questions each time the second user inputs or utters a response or question during an interactive conversational session. As another possibility, back-end platform 102 may receive the second user's responses and/or questions at some time after an interactive conversational session between the second user and the digital conversational character has ended. Back-end platform 102 may receive such conversational data at various other times as well.

At block 610, back-end platform 102 may then store the received conversational data in a given datastore (e.g., a datastore stored in data storage 204, or a datastore from an external data source). The stored conversational data may be used for various purposes.

For example, in some implementations, the stored conversational data may be indexed such that conversational data corresponding to interactions between the second user and the digital conversational character during the interactive conversational session can be referenced in a subsequent interactive conversational session between the second user and a digital conversational character. For instance, conversational data regarding a specific product (e.g., a prescription drug), date of last interaction, questions that were asked, and/or responses that were given during an interactive conversational session can be referenced in a subsequent interactive conversational session between the second user and a digital conversational character (which may be the same or different digital conversational character that interacted with the second user in a previous interactive conversational session). In one specific example, if the second user asks a question about an "itchy arm," then the phrase "itchy arm" may be classified as a "symptom" and stored as such. Similarly, in another specific example, if the second user asks a question about "penicillin," then the word "penicillin" may be classified as a "medicine" and stored as such. Back-end platform 102 may then reference the classified phrase "itchy arm" or word "penicillin" in a subsequent interactive conversational session involving the second user. In this respect, back-end platform 102 may be capable of querying historical conversations between the second user and a given digital conversational character, such that the second user may not have to repeat the same conversation it might have had in a previous interactive conversational session.

As another example, the stored conversational data may be used to update a set of conversational content that may be generated to define a given type of visual conversational application via the disclosed content authoring tool. In this respect, the first user (e.g., a professional) may then use the updated set of conversational content to define a given type of visual conversational application as described above.

As yet another example, the stored conversational data may be used to update a given predictive model (e.g., retrain the given predictive model) that is configured to predict whether a given response is appropriate for the digital conversational character based on a given question asked by the second user. In this respect, the given predictive model may improve over time as more interactive conversational sessions take place.

The stored conversational data may be used for various other purposes as well.

C. Example Rendering Phase Based on Object Detection

Method 1000 shown in FIG. 10 presents another embodiment of a method of the rendering phase that can be implemented within an operating environment including or involving, for example, the operating system 100 of FIG. 1, the computing platform 200 of FIG. 2A, and/or the computing device 201 of FIG. 2B. Method 400 may include one or more operations, functions, or actions as illustrated by one or more blocks 1002-1014. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

According to an example implementation, the rendering phase of the disclosed process may begin with the second user (e.g., a patient, a client, etc.) initiating, via the second user's computing device (e.g., computing device 114), an interactive conversational session with a digital conversational character. The second user may initiate an interactive conversational session with a digital conversational character in various manners.

As one example, in line with the discussion above, the second user may initiate an interactive conversational session with a digital conversational character by accessing, via the second user's computing device (e.g., computing device 114), a given type of visual conversation application that has been created by the first user (e.g., medical conversation application, interview conversation application, product conversation application, etc.). The second user may request access to the given type of visual conversation application in various manners described above.

In some implementations, the second user may initiate an interactive conversational session with a digital conversational character based on object detection. For instance, the second user may detect an object via the second user's computing device that may comprise a camera (e.g., camera 262), which may in turn trigger the second user's computing device to launch a given type of visual conversation application to initiate an interactive conversational session with a digital conversational character.

The second user may detect various types of objects via the second user's computing device. As one possibility, the second user may detect three-dimensional objects via the second user's computing device, examples of which may include a prescription bottle, a product (e.g., a toy, an electronic device, etc.), or a product packaging, among other objects. As another possibility, the second user may detect two dimensional objects via the second user's computing device, such as a two-dimensional image of an object, written text printed on an object, a business card, among other examples. The second user may detect various other types of objects as well.

Figure 11A:
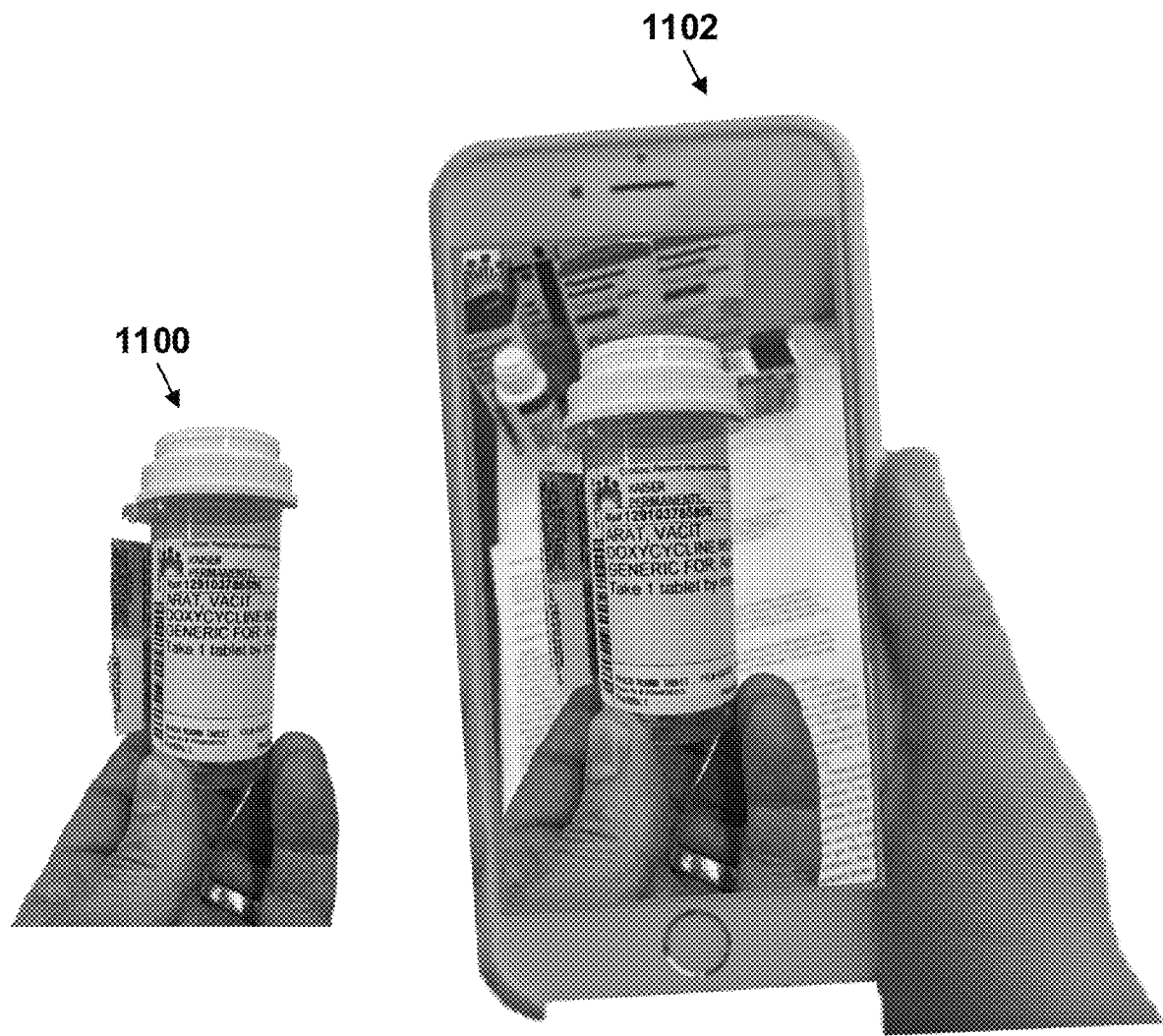
FIG. 11A depicts an example object that can be detected via a computing device in accordance with the present disclosure.

Further, an object may be detected via the second user's computing device in various manners. As one possibility, the second user may position the object in front of the second user's computing device that may comprise a camera (e.g., camera 262). The second user's computing device may then detect the object via the camera. To illustrate, FIG. 11A depicts a prescription bottle 1100 that comprises a prescription label that may be detected via computing device 1102 (which may be configured similarly to computing device 114). Computing device 1102 may detect the prescription bottle 1100 by positioning the prescription bottle 1100 in front of computing device 1102 that comprises a back-facing camera that can be used to detect prescription bottle 1100.

As another possibility, the second user may position the object in front of the second user's computing device that may comprise a camera (e.g., camera 262), and the second user may then take a picture of the object via the camera to detect the object. To illustrate, referring back to FIG. 11A, the second user may position prescription bottle 1100 in front of computing device 1102 that comprises a back-facing camera and take a picture of prescription bottle 1100. Computing device 1102 may then detect prescription bottle 1100.

As yet another possibility, the second user may launch a software application comprising a tool to detect objects. As one example, the second user may launch a given type of visual conversation application (e.g., the medical conversation application) that comprises a tool to detect objects. The tool may enable the second user to detect an object by positioning the object in front of the second user's computing device that comprises a camera and/or taking a picture of the object with the camera as described above.

In one implementation, in order to detect an object, the tool may require the second user to position the object within a bounded area presented in a view of the given type of visual conversation application. In another implementation, the tool may require the second user to position the object in front of the second user's computing device that comprises a camera and then rotate the object, such that various perspectives of the object can be captured.

As one example to illustrate, referring back to FIG. 11A, the second user may position prescription bottle 1100 in front of computing device 1102 that comprises a back-facing camera and rotate prescription bottle 1100 such that the camera can capture the entirety of the text on the prescription label of prescription bottle 1100. As the second user rotates prescription bottle 1100, the camera may capture the text on the prescription label in various manners.

As one possibility, the camera may capture the text on the prescription label by recording a video as the user rotates prescription bottle 1100. As another possibility, the camera may capture the text on the prescription label by taking one or more pictures of various perspectives of prescription bottle 1110 as the second user rotates prescription bottle 1100, where a given picture may be taken with or without user input.

In practice, the number of pictures that may be taken as the second user rotates an object may depend on the shape and size of the object. For instance, several pictures may be taken as the second user rotates prescription bottle 1110 in order to capture the small text on the prescription label that is wrapped around the curved surface of prescription bottle 1110. Further, in practice, while accessing the tool to detect an object, instructions may be presented to the second user that may include instructions to rotate the object in a particular manner and/or take a picture of a given perspective of the object, among other possible instructions.

It should be understood that computing device 1102 may comprise a front-facing camera, in which case an object (e.g., prescription bottle 1100) may be detected by placing the object between the second user and computing device 1102. Computing device 1102 may comprise various other cameras as well. Further, one of ordinary skill in the art will appreciate that various perspectives of an object may be captured in various other manners, and an object may be detected via the second user's computing device in various other manners well. For instance, instead of launching a given type of visual conversation application, the second user may launch a third-party software application comprising a tool to detect objects. One of ordinary skill in the art will also appreciate that the second user may initiate an interactive conversational session with a digital conversational character in various other manners as well.

At block 1002, back-end platform 102 may then receive, from the second user's computing device, data identifying the detected object. For instance, referring back to FIG. 11A, back-end platform 102 may receive one or more images and/or a video of prescription bottle 1100 from computing device 1102. Back-end platform 102 may receive data identifying a detected object at various times.

As one possibility, back-end platform 102 may receive data identifying the detected object upon detection of the object via the second user's computing device. As another possibility, back-end platform 102 may receive data identifying the detected object each time the second user takes a picture of the object with the second user's computing device. As yet another possibility, back-end platform 102 may receive data identifying the detected object after the second user inputs a selection via the second user's computing device to send such data. Back-end platform 102 may receive data identifying a detected object at various other times as well.

At block 1004, based on the received data identifying the detected object, back-end platform 102 may determine information associated with the detected object. Back-end platform 102 may determine information associated with the detected object in various manners. As one possibility, back-end platform 102 may determine information associated with the detected object using various image processing techniques, examples of which may include object recognition, image segmentation, video tracking, and optical character recognition, among other image processing techniques.

As one example to illustrate, referring back to FIG. 11A, based on the received data identifying prescription bottle 1100 that has been detected via computing device 1102, back-end platform 102 may determine prescription information associated with prescription bottle 1100, which may involve extracting the prescription information on the prescription label of prescription bottle 1100 using various image processing techniques mentioned above. Prescription information on a given prescription label may take various forms.

For example, prescription information on a given prescription label may comprise drug specific information. Drug specific information may generally include information about the prescription drug, such as a name of the drug, a dosage or strength of the drug, a manufacturer of the drug, a description of the drug, directions on how and when to take the drug, a quantity of the drug prescribed, an expiration date, and/or a date in which the drug was filled, a number of times the drug can be refilled, as some non-limiting examples.

As another example, prescription information on a given prescription label may comprise pharmacy specific information. Pharmacy specific information may generally include information about the pharmacy that filled the prescription, such as a name of the pharmacy, an address of the pharmacy, contact information (e.g., a phone number) for the pharmacy, a prescription number used by the pharmacy to identify the prescription that was filled, as some non-limiting examples.

As yet another example, prescription information on a given prescription label may comprise patient specific information. Patient specific information may generally include information about the patient, such as the name of the patient, an address of the patient, a name of the patient's doctor who prescribed the drug, as some non-limiting examples.

As a further example, prescription information on a given prescription label may comprise federal and/or state warning labels, which may depend on the type of drug that has been prescribed. For instance, depending on the type of drug that has been prescribed, prescription information on a given prescription label may comprise a warning label not to take the prescribed drug during pregnancy, a warning label not to drink alcohol while taking the prescribed drug, and/or a warning label that informs the patient that the prescribed drug may cause drowsiness or dizziness, among other warning labels.

Prescription information on a given prescription label may take various other forms as well.

In practice, prescription information on a given prescription label may be labeled in a specific format, which may depend on where the prescription was obtained (e.g., what pharmacy the prescription was obtained, the location of the pharmacy, etc.) and perhaps the type of drug that has been prescribed. In this respect, back-end platform 102 may be able to extract prescription information on a given prescription label based on the format of the given prescription label.

As one example to illustrate, FIG. 12 depicts prescription label 1200 for a given pharmacy (e.g., "Central Pharmacy") that includes prescription information that is organized in a specific format. As shown, prescription label 1200 may include prescription information comprising drug specific information in the middle portion of prescription label 12, including the name of the drug (e.g., "CLOZAPINE"), a dosage of the drug ("10-500MG"), a manufacturer of the drug ("FAZACLO"), directions on how and when to take the drug ("TAKE ONE TABLET ORALLY DAILY . . . "), a quantity of the drug prescribed ("24"), an expiration date ("USE BEFORE 06/24/12"), and/or a date in which the drug was filled ("06/24/10"), a number of times the drug can be refilled ("NO REFILLS"), as some non-limiting examples. As further shown in FIG. 12, prescription label 1200 may also include patient specific information above the directions on how and when to take the drug, pharmacy specific information in the top portion of prescription label 1200 above the patient specific information, and federal and/or state warning labels at the bottom of prescription label 1200.

In particular, back-end platform 102 may be able to extract prescription information on prescription label 1200 to determine prescription information associated with prescription label 1200. For instance, in one implementation, back-end platform 102 may extract a unique code on prescription label 1200 (e.g., the bar code on prescription label 1200, the prescription number "231-479-161" associated with the prescription, etc.) and look-up the unique code in a given datastore (e.g., a datastore stored in data storage 204, or a datastore from an external data source) to determine prescription information associated with prescription label 1200. In another implementation, back-end platform 102 may extract various prescription information on prescription label 1200 and based on the format of prescription label 1200, determine prescription information associated with prescription label 1200. In yet another implementation, back-end platform 102 may extract one or more key words on prescription label 1200 and look-up the extracted one or more key words in a given datastore to determine prescription information associated with prescription label 1200.

Back-end platform 102 may determine information associated with a detected object in various other manners as well. Further, while examples above have been described with respect to prescription label 1200, it should be understood that back-end platform 102 may be configured to determine information associated with various other objects as well. For instance, back-end platform 102 may be configured to determine information associated with a business card (name of an individual, address, organization name, contact information, occupation, organization logo, etc.) that may have been detected via the second user's computing device in similar manners described above with respect to prescription bottle 1200.

Figure 11B:
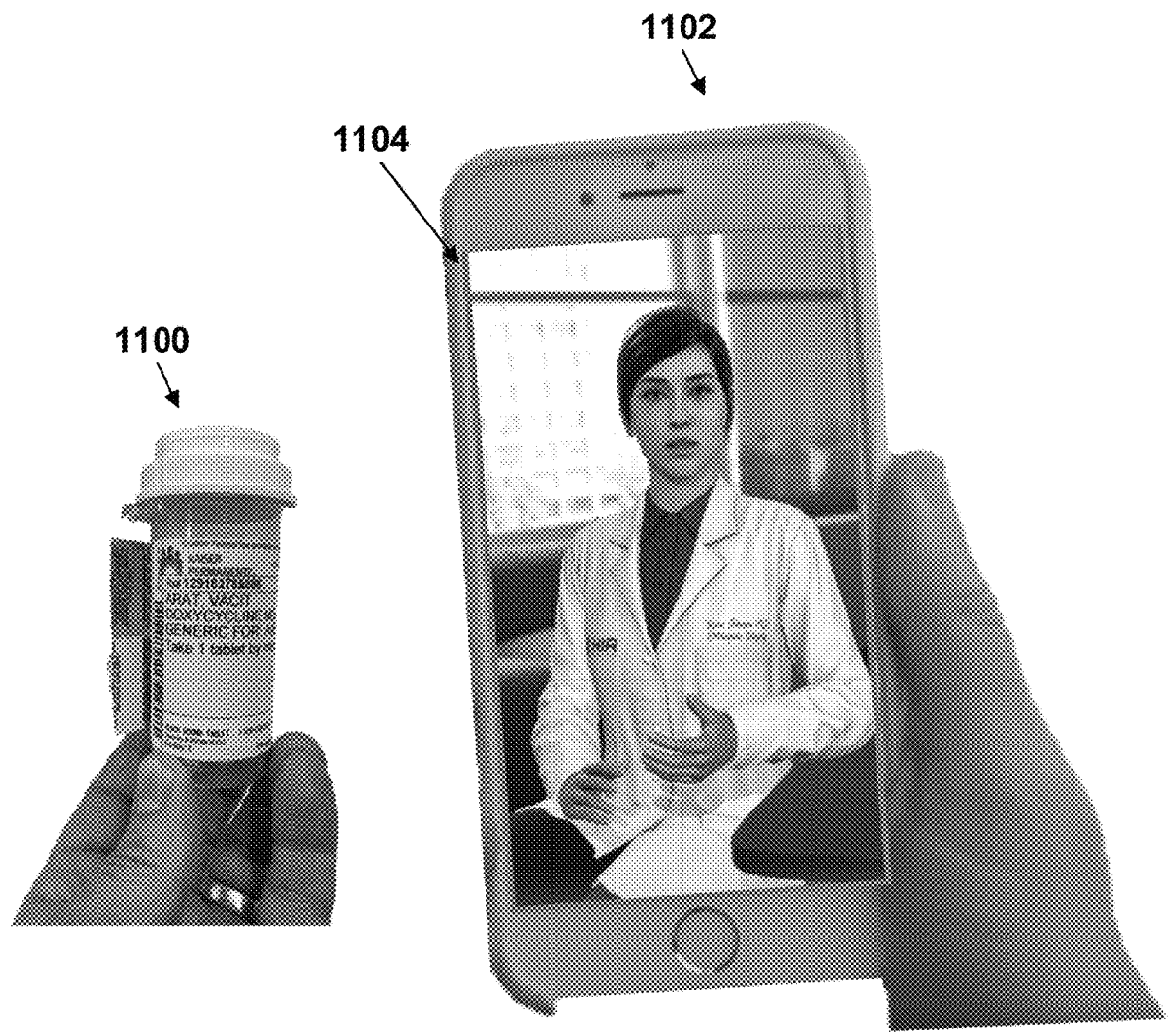
FIG. 11B depicts an example view of a given type of visual conversational application that may be presented to a computing device after detecting an object.

At block 1006, back-end platform 102 may cause the second user's computing device (e.g., computing device 114) to present a view of a given type of visual conversational application that enables the second user to interact with a digital conversational character in an interactive conversational session. For instance, as shown in FIG. 11B, after prescription bottle 1100 has been detected via computing device 1102, back-end platform 102 may cause computing device 1102 to present view 1104 of a medical conversation application.

In line with the discussion above with respect to block 602, back-end platform 102 may cause the second user's computing device to present a view of a given type of visual conversational application in various other manners, and the view may take various other forms as well.

In some implementations, before back-end platform 102 causes the second user's computing device to present a view of a given type of visual conversational application, back-end platform 102 may determine the given type of visual conversational application that should be presented based on the determined information associated with the detected object. For example, based on determining prescription information associated with a prescription label on a prescription bottle, back-end platform 102 may determine that the medical conversation application should be presented and then cause the second user's computing device to present a view of the medical conversational application. As another example, based on determining that information associated with a detected business card comprises a job title related to human resources, back-end platform 102 may determine that the interview conversation application should be presented and then cause the second user's computing device to present a view of the interview conversational application. It should be understood that depending on the determined information associated with a detected object, back-end platform 102 may determine that a different type of visual conversation application (e.g., product conversation application) should be presented.

At block 1008, at some point after determining information associated with the detected object, back-end platform 102 may optionally determine an interaction mode for an interactive conversational session between the second user and a digital conversational character. Back-end platform 102 may determine an interaction mode for an interactive conversational session between the second user and a digital conversational character in various manners.

As one possibility, back-end platform 102 may determine an interaction mode for an interactive conversational session based on the determined information associated with the detected object. For instance, back-end platform 102 may determine whether the information associated with the detected object corresponds to the second user. For example, back-end platform 102 may determine whether prescription information (e.g., patient specific information, such as the second user's last name, address, etc.) on a prescription label of a prescription bottle matches the second user's account information for a given type of visual conversation application. As another example, back-end platform 102 may determine whether information on a detected business card matches the second user's account information for a given type of visual conversation application.

In line with the discussion above with respect to block 604, back-end platform 102 may determine an interaction mode for an interactive conversational session between the second user and a digital conversational character in various other manners as well.

At block 1010, back-end platform 102 may then facilitate the interactive conversational session between the second user and the digital conversational character. For instance, in line with the discussion above with respect to block 606, back-end platform 102 may cause the digital conversational character to ask the second user a question or respond to the second user. Back-end platform 102 may also receive a second user's question or response during the interactive conversational session between the second user and the digital conversational character.

As one specific example, the second user may ask a question about a drug that has been prescribed to the second user (e.g., What are the side effects of this drug?). In response to the question, back-end platform 102 may use the determined prescription information associated with the detected prescription bottle (e.g., the name of the drug that has been prescribed) to look-up information about the drug in a given datastore (e.g., a datastore stored in data storage 204, or a datastore from an external data source) or perhaps the Internet (e.g., Food and Drug Administration's website or publicly searchable data source). Back-end platform 102 may then cause the digital conversational character to provide an appropriate response to the second user's question (e.g., side effects of clozapine are . . . ").

In some implementations, the digital conversational character may be configured to provide information during the interactive conversational session based on the location of the second user. For instance, if the second user is located near a pharmacy, the digital conversational character may be configured to provide various information associated with the pharmacy and perhaps associated with the second user (e.g., information about medication that has been prescribed for the second user at the pharmacy, information about the pharmacy's hours, information about a prescription that was filled for the second user at the pharmacy, etc.). Other examples involving other businesses are possible as well.

Further, in some implementations, in line with the discussion above, depending on the determined interaction mode, the digital conversational character may be configured to provide a different response to a question asked by the second user during an interactive conversational session. For instance, in personal mode, the digital conversational character may be configured to provide a response to a second user's question that includes patient specific information associated with a prescription label on a detected prescription bottle (e.g., prescription label 1200), possibly along with other types of prescription information (e.g., pharmacy specific information, drug specific information, etc.). In non-personal mode, digital conversational character may be configured to provide a response to a second user's question that includes prescription information associated with a prescription label on a detected prescription bottle (e.g., prescription label 1200), such as pharmacy specific information and/or drug specific information, but the digital conversational character may not be configured to provide a response to a second user's question that includes patient specific information.

For example, in personal mode, if the second user asks the question "When did my doctor prescribe the medication?" during the interactive conversational session, the digital conversational character may be configured to respond to the second user with the personal response, "Clozapin was prescribed to you by Dr. Jones on Jun. 24, 2010." In non-personal mode, if the second user asks the same question "When did my doctor prescribe the medication?" during the interactive conversational session, the digital conversational character may be configured to respond to the second user with the non-personal response "I am not allowed to answer that. Please ask a different question."

As another example, in personal mode, if the second user asks the question "Should I take this medicine before or after I eat?" during the interactive conversational session, the digital conversational character may be configured to respond to the second user with the personal response, "Dr. Jones prefers you to wait at least 30 minutes after you eat before taking clozapine, since you are also taking medication X." In non-personal mode, if the second user asks the same question "Should I take this medicine before or after I eat?" during the interactive conversational session, the digital conversational character may be configured to respond to the second user with the non-personal response "According to the drug manufacturer, you should take clozapine 15 minutes after you eat." Other examples are possible as well.

Further yet, in some implementations, depending on the determined interaction mode, a digital conversational character may be configured to take various actions for the second user in response to a second user's question/request during an interactive conversational session. For example, in personal mode, if the second user asks the question "I'm running low on my prescription, can you order more for me?" during the interactive conversational session, the digital conversational character may be configured to communicate with the second user's pharmacy to request a refill and confirm that a request to refill the prescription has been sent to the second user's pharmacy.

In practice, based on prescription information (e.g., patient specific information and/or drug specific information) associated with a detected prescription label on a prescription bottle, back-end platform 102 may determine whether it should request a refill for the second user. If back-end platform 102 determines that it should request a refill for the second user, then based on the pharmacy specific information associated with the detected prescription label on a prescription bottle, back-end platform 102 may communicate with a server associated with the pharmacy in order to request a refill for the second user. For instance, back-end platform 102 may send a prescription number and/or perhaps the patient's name on the prescription label (among other possible prescription information) to the server associated with the pharmacy, and back-end platform 102 may then receive a confirmation message indicating that a refill order has been placed. Back-end platform 102 may in turn cause the digital conversational character to notify the second user that a request to refill the prescription has been sent to the second user's pharmacy. If back-end platform 102 determines that it should not request a refill for the second user, in some implementations, back-end platform 102 may cause the digital conversational character to notify the second user that it is unable to request a refill.

In non-personal mode, if the second user asks the same question "I'm running low on my prescription, can you order more for me?" during the interactive conversational session, the digital conversational character may be configured to provide contact information for a pharmacy (based on the location of the second user or based on pharmacy specific information on the detected prescription label on a prescription bottle). In some implementations, the digital conversational character may be configured to notify the second user that it is unable to request a refill for the second user because it could not verify the prescription is for the second user.

Depending on the determined interaction mode, a digital conversational character may be configured to take various other actions for the second user in response to a second user's question/request during an interactive conversational session. For example, in personal mode, in response to a second user's question, the digital conversational character may be configured to schedule an appointment for the second user with the second user's doctor. In non-personal mode, in response to the same question, the digital conversational character may be configured to provide contact information of a given doctor's office. Depending on the determined interaction mode, a digital conversational character may be configured to take various other actions as well.

In some implementations, back-end platform 102 may change the determined interaction mode during the interactive conversational session between the second user and the digital conversational character. For instance, back-end platform 102 may transition from a personal mode to a non-personal mode if the second user asks the digital conversational character to refill a prescription during the interactive conversational session while logged into an account for "John Doe" but back-end platform 102 determines that the prescription is for "Jane Smith" based on prescription information associated with a detected prescription bottle. If the second user subsequently switches its account and logs into an account for "Jane Smith," back-end platform 102 may transition from the non-personal mode to the personal mode.

In other instances, back-end platform 102 may transition from a personal mode to a non-personal mode if the second user asks the digital conversational character to refill a prescription during the interactive conversational session while logged into an account for "John Doe" but back-end platform 102 determines that the prescription is for "Jane Smith," who is not a family member of John Doe, based on prescription information associated with a detected prescription bottle. If the second user subsequently switches its account and logs into an account for "Jane Smith" (or a family member of Jane Smith) back-end platform 102 may transition from the non-personal mode to the personal mode.

In practice, in line with the discussion above, back-end platform 102 may determine whether a first individual (e.g., Jane Smith) is a family member of a second individual (e.g., John Doe) by referencing account information associated with one of the individual's account and determining that the other individual is listed as a family member under the account. One of ordinary skill in the art will appreciate that back-end platform 102 may make such determination in various other manners as well (e.g., by referencing a given datastore).

Further, in some implementations, where multiple digital conversational characters are configured to interact with the second user during the interactive conversational session, a first digital conversational character may be configured to respond to certain types of information associated with the detected object (e.g., drug specific information associated with a detected prescription label on a prescription bottle) and a second digital conversational character may be configured to respond to different types information associate with the detected object (e.g., pharmacy specific information associated with the detected prescription label on a prescription bottle). In line with the discussion above, a transition phrase may be used to transition between different digital conversational characters.

One of ordinary skill in the art will appreciate that back-end platform 102 may facilitate the interactive conversational session between the second user and the digital conversational character in various other manners as well.

At block 1012, back-end platform 102 may receive, from the second user's computing device, conversational data corresponding to interactions between the second user and the digital conversational character. For instance, back-end platform 102 may receive the second user's responses to the digital conversational character's questions and/or the second user's questions asked during an interactive conversational session with the digital conversational character. In line with the discussion above with respect to block 608, back-end platform 102 may receive such conversational data at various times.

At block 1014, back-end platform 102 may then store the received conversational data in a given datastore (e.g., a datastore stored in data storage 204, or a datastore from an external data source). The stored conversational data may be used for various purposes described above with respect to block 610.

In some implementations, to protect the privacy of the second user, back-end platform 102 may not store certain conversational data received from the second user's computing device. For example, back-end platform 102 may not store patient-specific information in a given datastore to protect the privacy of the second user. In other implementations, back-end platform 102 may store such conversational data under the second user's account. In this respect, only users with the second user's account credentials may access such conversational data.

One of ordinary skill in the art will appreciate that back-end platform 102 may perform various other functions as well, which may depend in part on the detected object, information associated with the detected object, manner in which the first user interacts with the disclosed content authoring tool and/or the manner in which the second user interacts with a given type of visual conversation application.

Further, while an example implementation of the authoring phase has been described above with respect to a first user (e.g., a professional), it should be understood that any individual having access to the disclosed content authoring tool may create a given type of visual conversation application. Likewise, while an example implementation of the rendering phase has been described above with respect to a second user (e.g., a patient, a client, etc.), it should be understood that any individual having access to the given type of visual conversation application can interact with a digital conversational character in an interactive conversational session.

Further yet, while an example interactive conversational session has been described with respect to a single user (e.g., the second user) and a digital conversational character, it should be understood that an interactive conversational session may involve multiple users that may interact with a given digital conversational character during the same interactive conversational session.

One of ordinary skill in the art will appreciate that back-end platform 102 may perform various other functions as well, which may depend in part on the manner in which the first user interacts with the disclosed content authoring tool and/or the manner in which the second user interacts with a given type of visual conversation application.

Further, while an example implementation of the authoring phase has been described above with respect to a first user (e.g., a professional), it should be understood that any individual having access to the disclosed content authoring tool may create a given type of visual conversation application. Likewise, while an example implementation of the rendering phase has been described above with respect to a second user (e.g., a patient, a client, etc.), it should be understood that any individual having access to the given type of visual conversation application can interact with a digital conversational character in an interactive conversational session.

Further yet, while an example interactive conversational session has been described with respect to a single user (e.g., the second user) and a digital conversational character, it should be understood that an interactive conversational session may involve multiple users that may interact with a given digital conversational character during the same interactive conversational session.

V. CONCLUSION

Example embodiments of the disclosed innovations have been described above. Those skilled in the art will understand, however, that changes and modifications may be made to the embodiments described without departing from the true scope and spirit of the present invention, which will be defined by the claims.

Further, to the extent that examples described herein involve operations performed or initiated by actors, such as "humans," "users," or other entities, this is for purposes of example and explanation only. Claims should not be construed as requiring action by such actors unless explicitly recited in claim language.

What is claimed is:

1. A computing device comprising:
a network interface;
at least one processor;
a non-transitory computer-readable medium; and
program instructions stored on the non-transitory computer-readable medium that are executable by the at least one processor such that the computing device is configured to:
detect, via one or more sensors of the computing device, an object;
determine information associated with the detected object;
cause the computing device to present a view of a given type of visual conversation application that enables a user to interact with a digital conversational character in an interactive conversational session;
determine a given interaction mode from a plurality of interaction modes for the interactive conversational session between the user and the digital conversational character, wherein the plurality of interaction modes comprises a personal mode and a non-personal mode; and
facilitate the interactive conversational session between the user and the digital conversational character based on the determined information associated with the detected object and the determined interaction mode.

2. The computing device of claim 1, wherein the one or more sensors comprises a microphone, and wherein detecting the object comprises detecting sound signals associated with the object via the microphone.

3. The computing device of claim 1, wherein the one or more sensors comprises a camera, and wherein detecting the object comprises detecting the object via the camera.

4. The computing device of claim 3, wherein the object comprises a Quick Response (QR) code, and wherein detecting the object comprises detecting the QR code via the camera.

5. The computing device of claim 1, wherein the one or more sensors comprises a Global Positioning System (GPS), and wherein determining the information associated with the detected object comprises determining a location of the computing device that is near the detected object via the GPS.

6. The computing device of claim 1, wherein the computing device further comprises program instructions stored in the non-transitory computer-readable medium that are executable by the at least one processor such that the computing device is configured to:
launch the given type of visual conversation application.

7. The computing device of claim 1, wherein the computing device further comprises program instructions stored in the non-transitory computer-readable medium that are executable by the at least one processor such that the computing device is configured to:
cause the computing device to present a view of the given type of visual conversation application that enables the user to detect the object, wherein the view of the given type of visual conversation application that enables the user to detect the object comprises an indication on how to position the object.

8. The computing device of claim 1, wherein the given type of visual conversation application is a web application.

9. The computing device of claim 1, wherein determining the information associated with the detected object comprises:
sending data identifying the detected object from the computing device to a computing system; and
receiving the information associated with the detected object from the computing system.

10. The computing device of claim 1, wherein the digital conversational character comprises a digital representation of a human, an animal, an object, or a robot.

11. The computing device of claim 1, wherein the given type of visual conversation application comprises a medical conversation application that enables the user to interact with the digital conversational character during the interactive conversational session regarding medication.

12. The computing device of claim 1, wherein the object comprises a prescription bottle that includes a prescription label, and wherein determining the information associated with the detected object comprises extracting prescription information on the prescription label of the prescription bottle.

13. The computing device of claim 12, wherein the prescription information comprises one or more of drug specific information, pharmacy specific information, patient specific information, or warning information.

14. The computing device of claim 12, wherein extracting the prescription information on the prescription label of the prescription bottle comprises extracting a prescription number associated with the prescription label.

15. The computing device of claim 1, wherein determining the given interaction mode from the plurality of interaction modes for the interactive conversational session between the user and the digital conversational character comprises:
determining that the given interaction mode for the interactive conversational session should be in the personal mode based on determining that some of the information associated with the detected object matches information associated with an account of the user for the given type of visual conversation application.

16. The computing device of claim 1, wherein facilitating the interactive conversational session between the user and the digital conversational character comprises:
determining a given question that the digital conversational character should ask the user based on a location of the user;
based on the determination, causing the digital conversational character to utter the given question; and
receiving a response to the given question.

17. The computing device of claim 1, wherein facilitating the interactive conversational session between the user and the digital conversational character comprises:
receiving a given question regarding the detected object;
determining a response for the digital conversational character based on the given interaction mode and information associated with the detected object; and
causing the digital conversational character to utter the determined response to the given question.

18. The computing device of claim 1, wherein the detected object comprises a prescription bottle that includes a prescription label, and wherein facilitating the interactive conversational session between the user and the digital conversational character comprises:
receiving a given request to place an order to refill the prescription bottle;
determining that the given interaction mode comprises the non-personal mode;
based on the information associated with the detected prescription bottle, determining a pharmacy associated with the prescription bottle; and
based on determining (1) that the given interaction mode comprises the non-personal mode and (2) the pharmacy associated with the prescription bottle, causing the digital conversational character to utter a response to the given request comprising contact information for the pharmacy.

19. A method performed by a computing device, the method comprising:
detecting, via one or more sensors of the computing device, an object;
determining information associated with the detected object;
causing the computing device to present a view of a given type of visual conversation application that enables a user to interact with a digital conversational character in an interactive conversational session;
determining a given interaction mode from a plurality of interaction modes for the interactive conversational session between the user and the digital conversational character, wherein the plurality of interaction modes comprises a personal mode and a non-personal mode; and
facilitating the interactive conversational session between the user and the digital conversational character based on the determined information associated with the detected object and the determined interaction mode.

20. A non-transitory computer-readable storage medium, wherein the non-transitory computer-readable storage medium is provisioned with program instructions that are executable to cause a computing device to:
detect, via one or more sensors of the computing device, an object;
determine information associated with the detected object;
cause the computing device to present a view of a given type of visual conversation application that enables a user to interact with a digital conversational character in an interactive conversational session;
determine a given interaction mode from a plurality of interaction modes for the interactive conversational session between the user and the digital conversational character, wherein the plurality of interaction modes comprises a personal mode and a non-personal mode; and
facilitate the interactive conversational session between the user and the digital conversational character based on the determined information associated with the detected object and the determined interaction mode.

* * * * *